United States Patent
Fujiyama et al.

(10) Patent No.: US 9,574,218 B2
(45) Date of Patent: *Feb. 21, 2017

(54) METHOD OF CO-EXPRESSING GALACTOSYLTRANSFERASE AND A GLYCOPROTEIN IN A TRANSGENIC PLANT CELL AND SIALYLATING THE GLYCOPROTEIN FOR PRODUCTION OF GLYCOPROTEIN HAVING HUMAN-TYPE SUGAR CHAIN

(71) Applicant: Phyton Holdings, LLC, San Antonio, TX (US)

(72) Inventors: Kazuhito Fujiyama, Osaka (JP); Tatsuji Seki, Osaka (JP); Toshiomi Yoshida, Osaka (JP)

(73) Assignee: Phyton Holdings, LLC, Fort Worth, TX (US)

( * ) Notice: Subject to any disclaimer, the term of this patent is extended or adjusted under 35 U.S.C. 154(b) by 88 days.

This patent is subject to a terminal disclaimer.

(21) Appl. No.: 14/252,215

(22) Filed: Apr. 14, 2014

(65) Prior Publication Data
US 2014/0377799 A1    Dec. 25, 2014

Related U.S. Application Data

(60) Division of application No. 13/616,878, filed on Sep. 14, 2012, now Pat. No. 8,735,656, which is a continuation of application No. 12/836,925, filed on Jul. 15, 2010, now Pat. No. 8,309,795, which is a continuation of application No. 11/717,956, filed on Mar. 14, 2007, now abandoned, which is a continuation of application No. 10/466,941, filed as application No. PCT/JP02/00361 on Jan. 18, 2002, now abandoned.

(30) Foreign Application Priority Data

Jan. 19, 2001 (JP) .................................. 2001-012519

(51) Int. Cl.
    C12N 15/82      (2006.01)
    C12P 21/00      (2006.01)

(52) U.S. Cl.
    CPC ......... C12P 21/005 (2013.01); C12N 15/8257 (2013.01)

(58) Field of Classification Search
    None
    See application file for complete search history.

(56) References Cited

U.S. PATENT DOCUMENTS

| 4,956,282 A | 9/1990 | Goodman et al. |
|---|---|---|
| 5,202,422 A | 4/1993 | Hiatt et al. |
| 5,459,031 A | 10/1995 | Blumen et al. |
| 5,639,947 A | 6/1997 | Hiatt et al. |
| 5,874,271 A | 2/1999 | Nishikawa et al. |
| 5,879,912 A | 3/1999 | Roth |
| 5,939,288 A | 8/1999 | Thornburg |
| 5,955,282 A | 9/1999 | Hillman et al. |
| 5,959,177 A | 9/1999 | Hein et al. |
| 6,046,040 A | 4/2000 | Nishiguchi et al. |
| 6,054,304 A | 4/2000 | Taniguchi et al. |
| 6,331,418 B1 | 12/2001 | Roth |
| 6,344,600 B1 | 2/2002 | Merot et al. |
| 6,388,068 B1 | 5/2002 | Satoh et al. |
| 6,602,684 B1 | 8/2003 | Umana et al. |
| 6,653,459 B1 | 11/2003 | Von Schaewen et al. |
| 6,998,267 B1 * | 2/2006 | Seki ..................... C12N 9/0065 435/419 |
| 7,388,081 B2 * | 6/2008 | Seki ..................... C12N 9/0065 435/419 |
| 7,601,891 B2 | 10/2009 | Bakker et al. |
| 7,781,647 B2 | 8/2010 | Bakker et al. |
| 7,897,842 B2 | 3/2011 | Bakker et al. |
| 8,058,508 B2 | 11/2011 | Bakker et al. |
| 8,106,169 B2 | 1/2012 | Briggs et al. |
| 8,193,415 B2 | 6/2012 | Bakker et al. |

(Continued)

FOREIGN PATENT DOCUMENTS

| AU | 1681300 | 6/2000 |
|---|---|---|
| AU | 2012202479 | 5/2012 |

(Continued)

OTHER PUBLICATIONS

Chrispeels et al. The production of recombinant glycoproteins with defined non-immunogenic glycans. (1996) Transgenic Plants: A production system for Industrial and Pharmaceutical Proteins; pp. 99-113.*

Aoki et al. Golgi retention of a trans-Golgi membrane protein, galactosyl-transferase, requires cysteine and histidine residues within the membrane-anchoring domain. (1992) Cell Biology 89, 4319-4323.

Asano et al., Growth retardation and early death of beta-1,4-galactosyltransferase knockout mice with augmented proliferation and abnormal differentiation of epithelial cells. EMBO J. Apr. 15, 1997;16(8):1850-7.

Bailey et al. Metabolic engineering of N-linked glycoform synthesis systems in Chinese hamster ovary (CHO) cells (1997) Animal Cell Technology, pp. 489-494.

(Continued)

Primary Examiner — Cathy Kingdon Worley
(74) Attorney, Agent, or Firm — Wolf, Greenfield & Sacks, P.C.

(57) ABSTRACT

A method for the secretory production of a glycoprotein having a human-type sugar chain, comprising a step of introducing a gene of an enzyme capable of performing a transfer reaction of a galactose residue to a non-reducing terminal acetylglucosamine residue, and a gene of heterologous glycoprotein, to obtain a transformed plant cell, a step of culturing the plant cell, and a step of recovering the culture medium of the plant cell. The method further includes isolating the glycoprotein from the culture medium and contacting the isolated glycoprotein with a sialic acid transferase to add a sialic acid residue attached to the galactose residue in the N-glycan.

15 Claims, 24 Drawing Sheets

(56) References Cited

U.S. PATENT DOCUMENTS

| | | | |
|---|---|---|---|
| 8,241,909 B2* | 8/2012 | Seki | C12N 9/0065 435/419 |
| 8,309,795 B2* | 11/2012 | Fujiyama | C07K 14/47 435/419 |
| 8,492,613 B2 | 7/2013 | Bakker et al. | |
| 8,735,656 B2* | 5/2014 | Fujiyama | C07K 14/47 435/468 |
| 8,829,276 B2 | 9/2014 | Rouwendal et al. | |
| 8,853,370 B2* | 10/2014 | Seki | C12N 9/0065 530/380 |
| 8,907,163 B2 | 12/2014 | Bakker et al. | |
| 8,927,810 B2 | 1/2015 | Bakker et al. | |
| 9,255,277 B2 | 2/2016 | Bakker et al. | |
| 2001/0055584 A1 | 12/2001 | McKenzie et al. | |
| 2002/0019342 A1 | 2/2002 | Bayer | |
| 2002/0174453 A1 | 11/2002 | Danielle et al. | |
| 2004/0072290 A1 | 4/2004 | Umana et al. | |
| 2004/0181827 A1 | 9/2004 | Schaewen et al. | |
| 2004/0214273 A1 | 10/2004 | Fujiyama et al. | |
| 2005/0143564 A1 | 6/2005 | Seki et al. | |
| 2005/0144670 A1 | 6/2005 | Fujiyama et al. | |
| 2005/0223430 A1 | 10/2005 | Bakker et al. | |
| 2006/0253928 A1 | 11/2006 | Bakker et al. | |
| 2007/0089201 A1 | 4/2007 | Briggs et al. | |
| 2007/0214519 A1 | 9/2007 | Fujiyama et al. | |
| 2008/0003680 A1 | 1/2008 | Bakker et al. | |
| 2008/0034456 A1 | 2/2008 | Fujiyama et al. | |
| 2008/0124798 A1 | 5/2008 | Seki et al. | |
| 2010/0122365 A1 | 5/2010 | Bakker et al. | |
| 2011/0030108 A1 | 2/2011 | Bakker et al. | |
| 2011/0067146 A1 | 3/2011 | Rouwendal et al. | |
| 2011/0070649 A1 | 3/2011 | Seki et al. | |
| 2012/0010155 A1 | 1/2012 | Bakker et al. | |
| 2012/0011600 A1 | 1/2012 | Bakker et al. | |
| 2012/0036596 A9 | 2/2012 | Rouwendal et al. | |
| 2012/0060239 A1 | 3/2012 | Fujiyama et al. | |
| 2012/0210466 A9 | 8/2012 | Rouwendal et al. | |
| 2012/0237972 A1 | 9/2012 | Bakker et al. | |
| 2013/0040391 A1 | 2/2013 | Seki et al. | |
| 2013/0347146 A1 | 12/2013 | Bakker et al. | |
| 2015/0176020 A1 | 6/2015 | Rouwendal et al. | |

FOREIGN PATENT DOCUMENTS

| | | |
|---|---|---|
| DE | 19754622 | 6/1999 |
| EP | 0 351 313 A2 | 1/1990 |
| EP | 0 550 756 A1 | 7/1993 |
| EP | 0 737 745 A1 | 10/1996 |
| EP | 0 816 503 A1 | 1/1998 |
| EP | 1 243 647 A1 | 9/2002 |
| JP | S54-055790 | 5/1979 |
| JP | S56-016496 | 2/1981 |
| JP | S56-053696 | 5/1981 |
| JP | S56-108798 | 8/1981 |
| JP | S57-149228 | 9/1982 |
| JP | S57-169424 | 10/1982 |
| JP | H09-00261 | 1/1997 |
| JP | H09-84582 | 3/1997 |
| JP | H09-266792 | 10/1997 |
| JP | H10-313867 | 12/1998 |
| JP | H11-127890 | 5/1999 |
| JP | 2000-245470 | 9/2000 |
| JP | 2000-287692 | 10/2000 |
| JP | 2001-0333787 | 12/2001 |
| WO | WO 87/00865 | 2/1987 |
| WO | WO 92/18537 | 10/1992 |
| WO | WO 94/12646 | 6/1994 |
| WO | WO 95/02683 | 1/1995 |
| WO | WO 95/21248 | 8/1995 |
| WO | WO 97/04122 | 2/1997 |
| WO | WO 98/26053 | 6/1998 |
| WO | WO 98/31826 | 7/1998 |
| WO | WO 99/09187 | 2/1999 |
| WO | WO 99/24584 | 5/1999 |
| WO | WO 99/29879 | 6/1999 |
| WO | WO 99/38987 | 8/1999 |
| WO | WO 99/38990 | 8/1999 |
| WO | WO 99/51185 | 10/1999 |
| WO | WO 00/29603 | 5/2000 |
| WO | WO 00/34490 | 6/2000 |
| WO | WO 00/49153 | 8/2000 |
| WO | WO 00/52136 | 9/2000 |
| WO | WO 01/29241 | 4/2001 |
| WO | WO 01/29242 | 4/2001 |
| WO | WO 01/31044 | 5/2001 |
| WO | WO 01/31045 | 5/2001 |
| WO | WO 01/49821 | 7/2001 |
| WO | WO 01/49831 | 7/2001 |
| WO | WO 01/62912 | 8/2001 |
| WO | WO 01/64901 | 9/2001 |
| WO | WO 01/81591 | 11/2001 |
| WO | WO 01/82912 | 11/2001 |
| WO | WO 01/88143 | 11/2001 |
| WO | WO 02/00879 | 1/2002 |
| WO | WO 02/02793 | 1/2002 |
| WO | WO 02/057468 | 7/2002 |
| WO | WO 02/070672 | 9/2002 |
| WO | WO 03/011878 | 2/2003 |
| WO | WO 03/076614 | 9/2003 |
| WO | WO 03/078614 | 9/2003 |
| WO | WO 03/078637 | 9/2003 |
| WO | WO 2004/050838 | 6/2004 |

OTHER PUBLICATIONS

Bakker et al., An Arabidopsis thaliana Cdna complements the N-acetylglucosaminyltransferase I deficiency of CHO Lec1 cells. Biochem Biophys Res Commun. Aug. 11, 1999;261(3):829-32.

Bakker et al., Galactose-extended glycans of antibodies produced by transgenic plants. Proc Natl Acad Sci U S A. Feb. 27, 2001;98(5):2899-904.

Borisjuk et al., Production of Recombinant Proteins in Plant Root Exudates. Nat. Biotechnology 17(5): 466-469 (1999).

Boyd et al. The effect of the removal of sialic acid, galactose and total carbohydrate on the functional activity of Campath-1H (1995) Mol Imm. 32, 1311-8.

Cabanes-Macheteau et al., N-Glycosylation of a mouse IgG expressed in transgenic tobacco plants. Glycobiology. Apr. 1999;9(4):365-72.

Chen et al., Site-specific mutagenesis of Drosophila alcohol dehydrogenase: evidence for involvement of tyrosine-152 and lysine-156 in catalysis. Biochemistry. Apr. 6, 1993;32(13):3342-6.

Choi et al., Use of combinatorial genetic libraries to humanize N-linked glycosylation in the yeast Pichia pastoris. Proc Natl Acad Sci U S A. Apr. 29, 2003;100(9):5022-7. Epub Apr. 17, 2003.

Chrispeels and Faye, The production of recombinant glycoproteins with defined non-immunogenic glycans. In: Transgenic plants: a production system for industrial and pharmaceutical proteins. John Wiley Pub, UK. 1996:99-113.

Chrispeels, M., Glycobiology of Plant Cells, Essentials of Glycobiology, Ch. 20; Varki et al., 1st ed. (1999) Cold Spring Harbor Laboratory Press, NY.

Colley, Golgi localization of glycosyltransferases: more questions than answers. (1997) Glycobiology 7(1):1-13.

Cousin et al., Human variant sex hormone-binding globulin (SHBG) with an additional carbohydrate chain has a reduced clearance rate in rabbit. J Clin Endocrin Metab. 1998;83(1): 235-240.

Davies et al., Expression of GnTIII in a recombinant anti-CD20 CHO production cell line: Expression of antibodies with altered glycoforms leads to an increase in ADCC through higheraffinity for FC gamma RIII. Biotechnol Bioeng. Aug. 20, 2001;74(4):288-94.

De Vries et al. Isolation of total and polysomal RNA from plant tissues. (1991) Plant Mol. Biology B6/1-13.

Dieryck et al. Human Haemoglobin from transgenic tobacco (1997) Nature 386, 29-30.

Dinter and Berger, The regulation of cell- and tissue-specific expression of glycans by glycosyltransferases. Adv Exp Med Biol. 1995;376:53-82.

(56) References Cited

OTHER PUBLICATIONS

Elbers et al., Influence of growth conditions and developmental stage on N-glycan heterogeneity of transgenic immunoglobulin G and endogenous proteins in tobacco leaves. Plant Physiol. Jul. 2001;126(3):1314-22.

Essl et al., The N-terminal 77 amino acids from tobacco N-acetylglucosaminyltransferase I are sufficient to retain a reporter protein in the Golgi apparatus of Nicotiana benthamiana cells. FEBS Lett. Jun. 18, 1999;453(1-2):169-73.

Fast et al., The role of the carbohydrate chains of Gal beta-1,4-GlcNAc alpha 2,6-sialyltransferase for enzyme activity. Biochim Biophys Acta. Oct. 6, 1993;1202(2):325-30.

Faye et al., Affinity purification of antibodies specific for Asn-linked glycans containing alpha 1 --> 3 fucose or beta --> 2 xylose. (1993) Anal Biochem 209, 104-8.

Fischer and Evans, Molecular farming of pharmaceutical proteins. Transgenic Research. 2000;9:279-299.

Fischer et al., Molecular farming of recombinant antibodies in plants. (1999) Biol. Chem. 380: 825-839.

Fitchette Laine et al. N-glycans harboring the Lewis a epitope are expressed at the surface of plant cells. (1997) Plan J 12, 1411-7.

Fitchette-Laine et al., Chapter 19: Analysis of N- and O-Glycosylation of plant proteins. Methods in Biotechnology, vol. 3. Cunningham and Porter, eds. Humana Press. 1998: 271-90.

Florack et al., Expression of giant silkmoth cecropin B genes in tobacco. (1995) Transgenic Research 4, 132-141.

Fuchs et al., Purification and characterization of microbially expressed neomycin phosphotransferase II (NPTII) protein and its equivalence to the plant expressed protein. Biotechnology (N Y). Dec. 1993;11(13):1537-42.

Fujiyama et al., In vivo conversion of a glycan to human compatible type by transformed tobacco cells. Biochem Biophys Res Commun. Nov. 30, 2001;289(2):553-7.

Gasser and Fraley, Genetically Engineering Plants for Crop Improvement. Science. Jun. 16, 1989;244(4910):1293-1299.

Genbank Submission; Accession No. ADL27179. Hillman J. L. et al. May 20, 2004.

Genbank Submission; Accession No. BC124813. Aug. 5, 2006.

Genbank Submission; Accession No. Q08B99. Strausberg et al. Oct. 31, 2006.

Genbank Submission; Accession No. Q92074. Shaper J.H. Nov. 1, 1996.

Genbank Submission; Accession No. U19890. Shaper J. H. Aug. 3, 1996.

Genbank Submission; EMBL Database, Accession No. AJ277603. Bakker et al. Apr. 28, 2000.

Giddings, Transgenic plants as protein factories. Curr Opin Biotechnol. Oct. 2001;12(5):450-4.

Gleeson, Targeting of proteins to the Golgi apparatus. (1998) Histochem Cell Biol. 109: 517-532.

Gomez and Chrispeels, Complementation of an Arabidopsis thaliana mutant that lacks complex asparagine-linked glycans with the human cDNA encoding N-acetylglucosaminyltransferase I. Proc Natl Acad Sci U S A. Mar. 1, 1994;91(5):1829-33.

Grabenhorst and Conradt, The cytoplasmic, transmembrane, and stem regions of glycosyltransferases specify their in vivo functional sublocalization and stability in the Golgi. J Biol Chem. Dec. 17, 1999;274(51):36107-16.

Hamilton et al., Production of complex human glycoproteins in yeast. Science. Aug. 29, 2003;301(5637):1244-6.

Handa et al., The alpha 1→3 fucosylation at the penultimate GlcNAc catalyzed by fucosyltransferase VII is blocked by internally fucosylated residue in sialosyl long-chain poly-LacNAc: enzymatic basis for expression of physiological E-selectin epitope. Biochem Biophys Res Commun. Feb. 4, 1998;243(1):199-204.

Hein et al., Evaluation of immunoglobulins from plant cells. Biotechnol Prog. Sep.-Oct. 1991;7(5):455-61.

Herman and Horvitz, Three proteins involved in Caenorhabditis elegans vulval invagination are similar to components of a glycosylation pathway. Proc Natl Acad Sci U S A. Feb. 2, 1999;96(3):974-9.

Hess et al., Transformation experiments by pipetting Agrobacterium into the spikelets of wheat (*Triticum aestivum* L.). Plant Science 1990;72:233-44.

Hiei et al., Efficient transformation of rice (*Oryza sativa* L.) mediated by Agrobacterium and sequence analysis of the boundaries of the T-DNA. Plant J. Aug. 1994;6(2):271-82.

Hiei et al., Transformation of rice mediated by Agrobacterium tumefaciens. Plant Mol Biol. Sep. 1997;35(1-2):205-18.

Hollister et al. Stable expression of mammalian β1,4-galactosyltransferase extends the N-glycosylation pathway in insect cells. (1998) Glycobiology 8(5): 473-480.

Hollister et al., Engineering the protein N-glycosylation pathway in insect cells for production of biantennary, complex N-glycans. Biochemistry. Dec. 17, 2002;41(50):15093-104.

Horsch et al. A simple and general method for transferring genes into plants. (1985) Science 227, 1229-1231.

Huether et al., Glyco-engineering of moss lacking plant-specific sugar residues. Plant Biol (Stuttg). May 2005;7(3):292-9.

Ihara et al., cDNA cloning, expression, and chromosomal localization of human N-acetylglucosaminyltransferase III (GnT-III). J Biochem (Tokyo). Jun. 1993;113(6):692-8.

Ihara et al., Ectopic expression of N-acetylglucosaminyltransferase III in transgenic hepatocytes disrupts apolipoprotein B secretion and induces aberrant cellular morphology with lipid storage. Proc Natl Acad Sci USA. Mar. 1998; 95:2526-2530.

Ikeda et al., Kinetic basis for the donor nucleotide-sugar specificity of beta1, 4-N-acetylglucosaminyltransferase III. J Biochem. Oct. 2000;128(4):609-19.

Ioffe and Stanley, Mice lacking N-acetylglucosaminyltransferase I activity die at mid-gestation, revealing an essential role for complex or hybrid N-linked carbohydrates. Proc Natl Acad Sci U S A. Jan. 18, 1994;91(2):728-32.

Ishida et al., High efficiency transformation of maize (*Zea mays* L.) mediated by Agrobacterium tumefaciens. Nat Biotechnol. Jun. 1996;14(6):745-50.

Jähne et al., Genetic engineering of ceral crop plants: a review. Euphyica. Kluwer Academic Publishers. 1995:85:35-44.

James et al., Production and characterization of biologically active human GM-CSF secreted by genetically modified plant cells. Protein Expr Purif. Jun. 2000;19(1):131-8.

Jarvis and Finn, Modifying the insect cell N-glycosylation pathway with immediate early baculovirus expression vectors. (1996) Nat Biotechnol 14, 1288-92.

Jenkins et al., Getting the glycosylation right: implications for the biotechnology industry. Nat Biotechnol. Aug. 1996;14(8):975-81.

Johnson and Chrispeels, Substrate specificities of N-acetylglucosaminyl-, fucosyl-, and xylosyltransferases that modify glycoproteins in the Golgi apparatus of bean cotyledons. (1987) Plant Physiology 84, 1301-1308.

Kang et al. Salt tolerance of Arabidopsis thaliana requires maturation of N-glycosylated proteins in the Golgi apparatus. PNAS 2008 105(15):5933-5938.

Kawar et al., Insect cells encode a class II alpha-mannosidase with unique properties. J Biol Chem. May 11, 2001;276(19):16335-40. Epub Feb. 9, 2001.

Kieliszewski et al., Tandem mass spectrometry and structural elucidation of glycopeptides from a hydroxyproline-rich plant cell wall glycoprotein indicate that contiguous hydroxyproline residues are the major sites of hydroxyproline O-arabinosylation. J Biol Chem. Feb. 10, 1995;270(6):2541-9.

Kihlberg et al., Glysocylated peptide hormones: pharmacological properties and conformation studies of analogues of [1-Desamino,8-D-arginine]vasopressin. J Med Chem. 1995; 38(1):161-169. Abstract published Dec. 1, 1994.

Kitagawa et al., Molecular cloning and expression of glucuronyltransferase I involved in the biosynthesis of the glycosaminoglycan-protein linkage region of proteoglycans. J Biol Chem. Mar. 20, 1998;273(12):6615-8.

(56) References Cited

OTHER PUBLICATIONS

Kleene et al., Expression of soluble active human beta 1,4 galactosyltransferase in *Saccharomyces cerevisiae*. Biochem Biophys Res Commun. May 30, 1994;201(1):160-7.

Krezdorn et al., Human beta 1,4 galactosyltransferase and alpha 2,6 sialyltransferase expressed in *Saccharomyces cerevisiae* are retained as active enzymes in the endoplasmic reticulum. Eur J Biochem. Mar. 15, 1994;220(3):809-17.

Ku et al., High-level expression of maize phosphoenolpyruvate carboxylase in transgenic rice plants. Nat Biotechnol. Jan. 1999;17(1):76-80.

Leiter et al., Purification, cDNA cloning, and expression of GDP-L-Fuc:Asn-linked GlcNAc alpha1,3-fucosyltransferase from mung beans. J Biol Chem. Jul. 30, 1999;274(31):21830-9.

Lerouge et al., Control of the N-Glycosylation of therapeutic glycoproteins produced in transgenic plants: a new challenge for glycobiologists. Molecular Farming of Plants and Animals for Human and Veterinary Medicine. Chapter 4, 2002;73-109.

Lerouge et al., N-glycoprotein biosynthesis in plants: recent developments and future trends. Plant Mol Biol. Sep. 1998;38(1-2):31-48.

Lerouge et al., N-glycosylation of recombinant pharmaceutical glycoproteins produced in transgenic plants: towards an humanisation of plant N-glycans. Curr Pharm Biotechnol. Dec. 2000;1(4):347-54.

Li et al., Cloning, expression and characterization of a cDNA (6A8) encoding a novel human alpha-mannosidase. Eur J Biochem. Dec. 2000;267(24):7176-83. Erratum in: Eur J Biochem Nov. 2001;268(21):5653.

Ma et al. Generation and assembly of secretory antibodies in plants (1995) Science 268, 716-9.

Madson et al., Altered xyloglucans of arabidopsis thalianamutants bind normally to cellulose in vivo and in vitro. Poster from Plant Biology(Rockville) Jul. 27, 2001 Abstract #527.

Magnuson et al., Enhanced recovery of a secreted mammalian protein from suspension culture of genetically modified tobacco cells. Protein Expr Purif. Mar. 1996;7(2):220-8.

Magnuson et al., Secretion of biologically active human interleukin-2 and interleukin-4 from genetically modified tobacco cells in suspension culture. Protein Expr Purif. Jun. 1998;13(1):45-52.

Maras et al., In vitro conversion of the carbohydrate moiety of fungal glycoproteins to mammalian-type oligosaccharides—evidence for N-acetylglucosaminyltransferase-I-accepting glycans from Trichoderma reesei. Eur J Biochem. Nov. 1, 1997;249(3):701-7.

Masri et al., Identification of the full-length coding sequence for human galactosyltransferase (beta-N-acetylglucosaminide: beta 1,4-galactosyltransferase). Biochem Biophys Res Commun. Dec. 15, 1988;157(2):657-63.

Matsumoto et al., Characterization of a human glycoprotein (erythropoietin) produced in cultured tobacco cells. Mol. Biol. 1995; 27, 1163-1172.

Melo et al. Identification of the human Lewis(a) carbohydrate motif in a secretory peroxidase from a plant cell suspension culture (*Vaccinium myrtillus* L.) FEBS Lett. 1997; 415, 186-91.

Milland et al., The cytoplasmic tail of α1,2-fucosyltransferase contains a sequence for golgi localization. (2001) J. Biol. Chem. 276(15):12012-12018.

Miyake et al., Purification of human erythropoietin. J Biol Chem. Aug. 10, 1977;252(15):5558-64.

Miyoshi et al., The alpha1-6-fucosyltransferase gene and its biological significance. Biochim Biophys Acta. Dec. 6, 1999;1473(1):9-20.

Mokrzycki-Issartel et al., A transient tobacco expression system coupled to MALDI-TOF-MS allows validation of the impact of differential targeting on structure and activity of a recombinant therapeutic glycoprotein produced in plants. FEBS Lett. Sep. 25, 2003;552(2-3):170-6.

Munro, Localization of proteins to the Golgi apparatus. (1998) Trends Cell Biol. 8(1): 11-15.

Nagai et al., N-Glycosylation is Requisite for the Enzyme Activity and Golgi Retention of N-Acetylglucosaminyltransferase III. Glycobiology 7(6):769-776 (1997).

Palacpac et al., Stable expression of human beta1,4-galactosyltransferase in plant cells modifies N-linked glycosylation patterns. Proc Natl Acad Sci U S A. Apr. 13, 1999;96(8):4692-7.

Palacpac et al., Structures of N-linked oligosaccharides of glycoproteins from tobacco BY2 suspension cultured cells. Biosci Biotechnol Biochem. Jan. 1999;63(1):35-9.

Philipp et al., Characterization of nuclear membranes and endoplasmic reticulum isolated from plant tissue. JCB 1976 68:11-29.

Rayon et al., Characterization of N-Glycans from Arabidopsis. Application to a Fucose-Deficient Mutant (1999) Plant Physiology 119, 725-733.

Rayon et al., N-Glycosylation of phytohemagglutinin expressed in bean cotyledons or in transgenic tobacco plants. Plant Physiol Biochem. 1996;34:273-81.

Rayon et al., The protein N-glycosylation in plants. Journal Exper Botany. Sep. 1998. 49(326):1463-72.

Rishi et al., Molecular Farming in Plants: A Current Perspective. (2001) J. Plant Biochem. & Biotech 10: 1-12.

Rothman, Protein sorting by selective retention in the endoplasmic reticulum and Golgi stack. Cell. Aug. 14, 1987;50(4):521-2.

Saint-Jore-Dupas et al. "Plant N-Glycan Processing Enzymes Employ Different Targeting Mechanisms for Their Spatial Arrangement along the Secretory Pathway." The Plant Cell 2006 18:3182-3200.

Saito et al., Integration and expression of a rabbit liver cytochrome P-450 gene in transgenic Nicotiana tabacum (1991) Proc. Natl. Acad. Sci. 88, 7041-7045.

Sakai et al., Fatty Acid acylation of apoE by human monocyte/marophages and heptocytes. Apr. 1998; 417. Abstract.

Sakai et al., Human glycosyltransferase expression and intracellular/intercellular glycoprotein sugar chain structure in cultured tobacco BY2 cells. IC Biotech. Osaska, Nara Institute. Mar. 1998. Abstract. Original with English Abstract.

Schachter, The 'yellow brick road' to branched complex N-glycans. Glycobiology. Nov. 1991;1(5):453-61.

Scherer et al., Action and Inhibition of Endogenous Phospholipases during Isolation of Plant Membranes. Plant Physiol 1978 62:933-37.

Schindler et al., Arabinogalactan proteins in maize coleoptiles: developmental relationship to cell death during xylem differentiation but not to extention growth. (1995) Plant JU v7, 25-36.

Seveno et al., Glycoprotein Sialylation in plants? Nat Biotechnol. Nov. 2004;22(11):1351-2.

Shah et al., Sialylated endogenous glycoconjugates in plant cells. Nat Biotechnol. Dec. 2003;21(12):1470-1. Epub Nov. 9, 2003.

Shaper et al., Bovine galactosyltransferase: identification of a clone by direct immunological screening of a cDNA expression library. (1986) Proc Natl Acad Sci USA v83, 1573-7.

Smant et al., Potato root diffusate-induced secretion of soluble, basic proteins originating from the subventral esophageal glands of potato cyst nematodes (1997) Phytopathology v87, 839-845.

Sourrouille et al., Down-regulated expression of plant-specific glycoepitopes in alfalfa. Plant Biotechnol J. Sep. 2008;6(7):702-21.

Stanley et al., CHO cells provide access to novel N-glycans and developmentally regulated glycosyltransferases. Glycobiology. 1996;6:695-9.

Stanley et al., Glycosyltransferase mutants: key to new insights in glycobiology. FASEB J. 1995;9:1436-44.

Staudacher et al., Functional purification and characterization of a GDP-fucose: beta-N-acetylglucosamine (Fuc to Asn linked GlcNAc) alpha 1,3-fucosyltransferase from mung beans. Glycoconj J. Dec. 1995;12(6):780-6.

Staudacher et al., Strict order of (Fuc to Asn-linked GlcNAc) fucosyltransferases forming core-difucosylated structures. Glycoconj J. Apr. 1998;15(4):355-60.

Strasser et al., Molecular basis of N-acetylglucosaminyltransferase I deficiency in Arabidopsis thaliana plants lacking complex N-glycans. Biochem J. Apr. 15, 2005;387(Pt 2):385-91. Epub Nov. 10, 2004.

(56) References Cited

OTHER PUBLICATIONS

Strasser et al., Molecular cloning and functional expression of beta 1,2-sylosyltransferase cDNA from Arabidopsis thalianal. Febs Letters, Elsvier, Amsterdam, NL, Apr. 2000 472(1): 105-108.
Strasser et al., Molecular cloning of cDNA encoding N-acetylglucosaminyltransferase II from Arabidopsis thaliana. Glycoconj J. Dec. 1999;16(12):787-91.
Sturm et al., Subcellular localization of glycosidases and glycosyltransferases involved in the processing of N-linked oligosaccharides. (1987) Plant Physiol. 85(3):741-745.
Takahashi et al., Xylose-containing common structural unit in N-linked oligosaccharides of laccase from sycamore cells. Biochemistry. 1986;25(2):388-95.
Tang et al., The transmembrane domain of N-glucosaminyltransferase I contains a Golgi retention signal. J Biol Chem. May 15, 1992;267(14):10122-6.
Taniguchi et al., A glycomic approach to the identification and characterization of glycoprotein function in cells transfected with glycosyltransferase genes. Proteomics. Feb. 2001;1(2):239-47.
Terashima et al., Effect of Osmotic Pressure on Human α1-Antitrypsin Production by Plant Cell Culture. Biochemical Engineering Journal 4 (1999) 31-36.
Terayama et al., Cloning and functional expression of a novel glucuronyltransferase involved in the biosynthesis of the carbohydrate epitope HNK-1. Proc Natl Acad Sci U S A. Jun. 10, 1997;94(12):6093-8.
Terayama et al., Purification and characterization of a glucuronyltransferase involved in the biosynthesis of the HNK-1 epitope on glycoproteins from rat brain. J Biol Chem. Nov. 13, 1998;273(46):30295-30300.
Thanavala et al. Immunogenicity of transgenetic plant derived hepatitis B surface antigen. (1995) Proc Natl Acad Sci USA 92, 3358-3361.
Udagama-Randeniya et al., Electrophoretic analysis of coniferyl alcohol oxidase and related laccases. Electrophoresis. Aug.-Sep. 1994;15(8-9):1072-7.
Umana et al., Engineered glycoforms of an antineuroblastoma IgG1 with optimize antibody-dependent cellular cytotoxic activity. (1999) Nature Biotech. 17: 176-180.
Van Engelen et al., pBINPLUS: an improved plant transformation vector based on pBIN19. (1995) Transgenetic Res 4, 288-90.
Van Engelen et al., Coordinate expression of antibody subunit genes yields high levels of functional antibodies in roots of transgenic tobacco. Plant Mol Biol. Dec. 1994;26(6):1701-10.
Van Ree et al., Beta(1,2)-xylose and alpha(1,3)-fucose residues have a strong contribution in IgE binding to plant glycoallergens. J Biol Chem. Apr. 14, 2000;275(15):11451-8.
Vitale and Chrispeels, Transient N-acetylglucosamine in the biosynthesis of phytohemagglutinin: attachment in the Golgi apparatus and removal in protein bodies. J Cell Biol. Jul. 1984;99(1 Pt 1):133-40.
Voelker et al., In vitro mutated phytohemagglutinin genes expressed in tobacco seeds: role of glycans in protein targeting and stability. Plant Cell. Jan. 1989;1(1):95-104.
Von Schaewen et al., Isolation of a mutant arabidopsis plant that lacks N-acetyl glucosaminyl transferase I and is unable to synthesize Golgi-modified complex N-linked glycans. (1993) Plant Physiol 102, 1109-18.
Warner, Metabolic engineering glycosylation: biotechnology's challenge to the glycobiologist in the next millenium; Carbohydrates in chemistry and biology, part II vol. 4. editors Earnst et al. (2000) Wiley-VCH. 1042-64.
Wee et al., Targeting of active sialyltransferase to the plant Golgi apparatus. Plant Cell. Oct. 1998;10(10):1759-68.
Whitelam, The production of recombinant proteins in plants. (1995) J. Sci. Food Agric., 68:1-9.
Wiebauer et al., Nuclear pre-mRNA processing in plants: distinct modes of 3' splice-site selection in plants and animals (1988) MCB: vol. 8 pp. 2042-2051.
Wilson et al., Cloning and expression of cDNAs encoding alpha1,3-fucosyltransferase homologues from Arabidopsis thaliana. Biochim Biophys Acta. Jul. 2, 2001;1527(1-2):88-96.
Wilson et al., Core alpha1,3-fucose is a key part of the epitope recognized by antibodies reacting against plant N-linked oligosaccharides and is present in a wide variety of plant extracts. Glycobiology. Jul. 1998;8(7):651-61.
Wright and Morrison, Effect of glycosylation on antibody function: implications for genetic engineering. Trends Biotechnol. Jan. 1997;15(1):26-32.
Yamaguchi and Fukuda Golgi retention mechanism of β-1,4-Galactosyltransferase (1995) J of Biol Chemistry 270(20): 12170-12176.
Yamaguchi et al., Genomic structure and promoter analysis of the human alpha1, 6-fucosyltransferase gene (FUT8). Glycobiology. Jun. 2000;10(6):637-43.
Yin et al., [Obtaining transgenic rice plants and their progenies using Agrobacterium tumefaciens] Yi Chuan Xue Bao. Dec. 1998;25(6):517-24. Chinese. English abstract only.
Yoshida et al., Expression of β1 4 galactosyltransferase in tobacco culture cell. Program for Congress of the Society for Bioscience and Bioengineering of Japan. Sep. 15, 1995;1-5.
Yoshida et al., Molecular biology and application of plant peroxidase genes. Appl Microbiol Biotechnol. Feb. 2003;60(6):665-70. Epub Dec. 18, 2002.
Yosida et al., Challenge for production of human-compatible glycoprotein therapeutics in yeast. Bioscience and Industry. 1996;54(6): 420-422.
Zhang and Wang, Quantitative analysis and process monitoring of site-specific glycosylation microheterogeneity in recombinant human interferon-gamma from Chinese hamster ovary cell culture by hydrophilic interaction chromatography. J Chromatogr B Biomed Sci Appl. Aug. 7, 1998;712(1-2):73-82.
Zhang et al., Agrobacterium-mediated transformation of elite indica and japonica rice cultivars. Mol Biotechnol. Dec. 1997;8(3):223-31.
Zhang et al., Transformation of tobacco using human β-1 , 4 galactosyltransferase gene and regeneration of transgenic plants. Annual reports of IC Biotech. 1995;18:241-7.
Zhu et al., Beta 1,4 N-acetylgalactosaminyltransferase (GM2/GD2/GA2 synthase) forms homodimers in the endoplasmic reticulum: a strategy to test for dimerization of Golgi membrane proteins. Glycobiology. Oct. 1997;7(7):987-96.
Genbank Submission; Accession No. AA124814. Strausberg et al. Oct. 27, 2006.
Kitada et al., The addition of bisecting N-acetylglucosamine residues to E-cadherin down-regulates the tyrosine phosphorylation of beta-catenin. J Biol Chem. Jan. 5, 2001;276(1):475-80.
Sakai et al., Journal of the Japan Society for Bioscience, Biotechnology and Agrochemistry, Collected Abstract. Annual Conference of the Japan Society for Bioscience, Biotechnology and Agrochemistry. Mar. 5, 1998;72:164 Abstract 2D1p20.

* cited by examiner

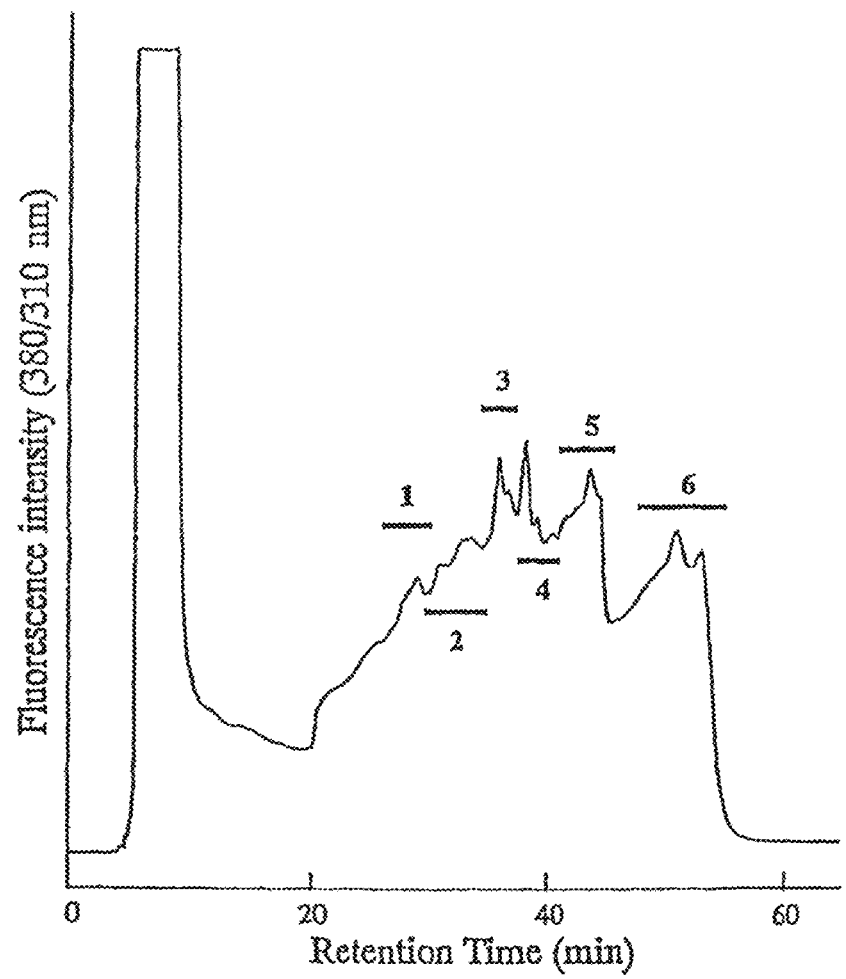

A, C ; Gal GN M3 (19.6%)

B, D ; Gal GN M3X (35.2%)

E ; Gal GN M4 (18.4%)

F ; Gal GN M5 (26.8%)

MW; Protein Molecular Weight Marker (Daiichi Kagaku yakuhin)

SEQUENCE LISTING

```
<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:primer
      hGT-5Eco

<400> SEQUENCE: 1
```

```
aaagaattcg cgatgccagg cgcgcgtccc t                                    31

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:primer
      hGT-2Sal

<400> SEQUENCE: 2
tcgatcgcaa aaccatgtgc agctgatg                                        28

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:primer
      hGT-7Spe

<400> SEQUENCE: 3
acgggactcc tcagggggcga tgatcataa                                      29

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:primer
      hGT-6Spe

<400> SEQUENCE: 4
aagactagtg ggccccatgc tgattga                                         27

<210> SEQ ID NO 5
<211> LENGTH: 1158
<212> TYPE: DNA
<213> ORGANISM: Homo sapiens
<220> FEATURE:
<221> NAME/KEY: CDS
<222> LOCATION: (1)..(1155)

<400> SEQUENCE: 5 atg cca ggc gcg tcc cta cag cgg gcc tgc cgc ctg ctc gtg gcc gtc     48
Met Pro Gly Ala Ser Leu Gln Arg Ala Cys Arg Leu Leu Val Ala Val
 1               5                  10                  15 tgc gct ctg cac ctt ggc gtc acc ctc gtt tac tac ctg gct ggc cgc     96
Cys Ala Leu His Leu Gly Val Thr Leu Val Tyr Tyr Leu Ala Gly Arg
                20                  25                  30 gac ctg agc cgc ctg ccc caa ctg gtc gga gtc tcc aca ccg ctg cag    144
Asp Leu Ser Arg Leu Pro Gln Leu Val Gly Val Ser Thr Pro Leu Gln
            35                  40                  45 ggc ggc tcg aac agt gcc gcc gcc atc ggg cag tcc tcc ggg gag ctc    192
Gly Gly Ser Asn Ser Ala Ala Ala Ile Gly Gln Ser Ser Gly Glu Leu
        50                  55                  60 cgg acc gga ggg gcc cgg ccg ccg cct cct cta ggc gcc tcc tcc cag    240
Arg Thr Gly Gly Ala Arg Pro Pro Pro Pro Leu Gly Ala Ser Ser Gln
 65                  70                  75                  80 ccg cgc ccg ggt ggc gac tcc agc cca gtc gtg gat tct ggc cct ggc    288
Pro Arg Pro Gly Gly Asp Ser Ser Pro Val Val Asp Ser Gly Pro Gly
                85                  90                  95 ccc gct agc aac ttg acc tcg gtc cca gtg ccc cac acc acc gca ctg    336
Pro Ala Ser Asn Leu Thr Ser Val Pro Val Pro His Thr Thr Ala Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 100 |     |     |     |     | 105 |     |     |     |     | 110 |     |     |      |
| tcg | ctg | ccc | gcc | tgc | cct | gag | gag | tcc | ccg | cta | cta | gtg | ggc | ccc | atg | 384  |
| Ser | Leu | Pro | Ala | Cys | Pro | Glu | Glu | Ser | Pro | Leu | Leu | Val | Gly | Pro | Met |      |
|     |     | 115 |     |     |     |     | 120 |     |     |     |     | 125 |     |     |     |      |
| ctg | att | gag | ttt | aac | atg | cct | gtg | gac | ctg | gag | ctc | gtg | gca | aag | cag | 432  |
| Leu | Ile | Glu | Phe | Asn | Met | Pro | Val | Asp | Leu | Glu | Leu | Val | Ala | Lys | Gln |      |
|     | 130 |     |     |     |     | 135 |     |     |     |     | 140 |     |     |     |     |      |
| aac | cca | aat | gtg | aag | atg | ggc | ggc | cgc | tat | gcc | ccc | agg | gac | tgc | gtc | 480  |
| Asn | Pro | Asn | Val | Lys | Met | Gly | Gly | Arg | Tyr | Ala | Pro | Arg | Asp | Cys | Val |      |
| 145 |     |     |     |     | 150 |     |     |     |     | 155 |     |     |     |     | 160 |      |
| tct | cct | cac | aag | gtg | gcc | atc | atc | att | cca | ttc | cgc | aac | cgg | cag | gag | 528  |
| Ser | Pro | His | Lys | Val | Ala | Ile | Ile | Ile | Pro | Phe | Arg | Asn | Arg | Gln | Glu |      |
|     |     |     | 165 |     |     |     |     | 170 |     |     |     |     | 175 |     |     |      |
| cac | ctc | aag | tac | tgg | cta | tat | tat | ttg | cac | cca | gtc | ctg | cag | cgc | cag | 576  |
| His | Leu | Lys | Tyr | Trp | Leu | Tyr | Tyr | Leu | His | Pro | Val | Leu | Gln | Arg | Gln |      |
|     |     | 180 |     |     |     |     | 185 |     |     |     |     | 190 |     |     |     |      |
| cag | ctg | gac | tat | ggc | atc | tat | gtt | atc | aac | cag | gcg | gga | gac | act | ata | 624  |
| Gln | Leu | Asp | Tyr | Gly | Ile | Tyr | Val | Ile | Asn | Gln | Ala | Gly | Asp | Thr | Ile |      |
|     - | 195 |     |     |     |     | 200 |     |     |     |     | 205 |     |     |     |     |      |
| ttc | aat | cgt | gct | aag | ctc | ctc | aat | gtt | ggc | ttt | caa | gaa | gcc | ttg | aag | 672  |
| Phe | Asn | Arg | Ala | Lys | Leu | Leu | Asn | Val | Gly | Phe | Gln | Glu | Ala | Leu | Lys |      |
|     | 210 |     |     |     |     | 215 |     |     |     |     | 220 |     |     |     |     |      |
| gac | tat | gac | tac | acc | tgc | ttt | gtg | ttt | agt | gac | gtg | gac | ctc | att | cca | 720  |
| Asp | Tyr | Asp | Tyr | Thr | Cys | Phe | Val | Phe | Ser | Asp | Val | Asp | Leu | Ile | Pro |      |
| 225 |     |     |     |     | 230 |     |     |     |     | 235 |     |     |     |     | 240 |      |
| atg | aat | gac | cat | aat | gcg | tac | agg | tgt | ttt | tca | cag | cca | cgg | cac | att | 768  |
| Met | Asn | Asp | His | Asn | Ala | Tyr | Arg | Cys | Phe | Ser | Gln | Pro | Arg | His | Ile |      |
|     |     |     |     | 245 |     |     |     |     | 250 |     |     |     |     | 255 |     |      |
| tcc | gtt | gca | atg | gat | aag | ttt | gga | ttc | agc | cta | cct | tat | gtt | cag | tat | 816  |
| Ser | Val | Ala | Met | Asp | Lys | Phe | Gly | Phe | Ser | Leu | Pro | Tyr | Val | Gln | Tyr |      |
|     |     |     | 260 |     |     |     |     | 265 |     |     |     |     | 270 |     |     |      |
| ttt | gga | ggt | gtc | tct | gct | cta | agt | aaa | caa | cag | ttt | cta | acc | atc | aat | 864  |
| Phe | Gly | Gly | Val | Ser | Ala | Leu | Ser | Lys | Gln | Gln | Phe | Leu | Thr | Ile | Asn |      |
|     |     | 275 |     |     |     |     | 280 |     |     |     |     | 285 |     |     |     |      |
| gga | ttt | cct | aat | aat | tat | tgg | ggc | tgg | gga | gga | gaa | gat | gat | gac | att | 912  |
| Gly | Phe | Pro | Asn | Asn | Tyr | Trp | Gly | Trp | Gly | Gly | Glu | Asp | Asp | Asp | Ile |      |
|     | 290 |     |     |     |     | 295 |     |     |     |     | 300 |     |     |     |     |      |
| ttt | aac | aga | tta | gtt | ttt | aga | ggc | atg | tct | ata | tct | cgc | cca | aat | gct | 960  |
| Phe | Asn | Arg | Leu | Val | Phe | Arg | Gly | Met | Ser | Ile | Ser | Arg | Pro | Asn | Ala |      |
| 305 |     |     |     |     | 310 |     |     |     |     | 315 |     |     |     |     | 320 |      |
| gtg | gtc | ggg | agg | tgt | cgc | atg | atc | cgc | cac | tca | aga | gac | aag | aaa | aat | 1008 |
| Val | Val | Gly | Arg | Cys | Arg | Met | Ile | Arg | His | Ser | Arg | Asp | Lys | Lys | Asn |      |
|     |     |     | 325 |     |     |     |     | 330 |     |     |     |     | 335 |     |     |      |
| gaa | ccc | aat | cct | cag | agg | ttt | gac | cga | att | gca | cac | aca | aag | gag | aca | 1056 |
| Glu | Pro | Asn | Pro | Gln | Arg | Phe | Asp | Arg | Ile | Ala | His | Thr | Lys | Glu | Thr |      |
|     |     | 340 |     |     |     |     | 345 |     |     |     |     | 350 |     |     |     |      |
| atg | ctc | tct | gat | ggt | ttg | aac | tca | ctc | acc | tac | cag | gtg | ctg | gat | gta | 1104 |
| Met | Leu | Ser | Asp | Gly | Leu | Asn | Ser | Leu | Thr | Tyr | Gln | Val | Leu | Asp | Val |      |
|     |     |     | 355 |     |     |     |     | 360 |     |     |     |     | 365 |     |     |      |
| cag | aga | tac | cca | ttg | tat | acc | caa | atc | aca | gtg | gac | atc | ggg | aca | ccg | 1152 |
| Gln | Arg | Tyr | Pro | Leu | Tyr | Thr | Gln | Ile | Thr | Val | Asp | Ile | Gly | Thr | Pro |      |
|     | 370 |     |     |     |     | 375 |     |     |     |     | 380 |     |     |     |     |      |
| agc | tag |     |     |     |     |     |     |     |     |     |     |     |     |     |     | 1158 |
| Ser |     |     |     |     |     |     |     |     |     |     |     |     |     |     |     |      |
| 385 |     |     |     |     |     |     |     |     |     |     |     |     |     |     |     |      |

<210> SEQ ID NO 6
<211> LENGTH: 385
<212> TYPE: PRT
<213> ORGANISM: Homo sapiens

<400> SEQUENCE: 6

```
Met Pro Gly Ala Ser Leu Gln Arg Ala Cys Arg Leu Val Ala Val
  1               5                  10                  15

Cys Ala Leu His Leu Gly Val Thr Leu Val Tyr Tyr Leu Ala Gly Arg
             20                  25                  30

Asp Leu Ser Arg Leu Pro Gln Leu Val Gly Val Ser Thr Pro Leu Gln
             35                  40                  45

Gly Gly Ser Asn Ser Ala Ala Ala Ile Gly Gln Ser Ser Gly Glu Leu
 50                  55                  60

Arg Thr Gly Gly Ala Arg Pro Pro Pro Leu Gly Ala Ser Ser Gln
 65                  70                  75                  80

Pro Arg Pro Gly Gly Asp Ser Ser Pro Val Val Asp Ser Gly Pro Gly
             85                  90                  95

Pro Ala Ser Asn Leu Thr Ser Val Pro Val Pro His Thr Thr Ala Leu
             100                 105                 110

Ser Leu Pro Ala Cys Pro Glu Glu Ser Pro Leu Leu Val Gly Pro Met
             115                 120                 125

Leu Ile Glu Phe Asn Met Pro Val Asp Leu Glu Leu Val Ala Lys Gln
130                 135                 140

Asn Pro Asn Val Lys Met Gly Gly Arg Tyr Ala Pro Arg Asp Cys Val
145                 150                 155                 160

Ser Pro His Lys Val Ala Ile Ile Ile Pro Phe Arg Asn Arg Gln Glu
             165                 170                 175

His Leu Lys Tyr Trp Leu Tyr Tyr Leu His Pro Val Leu Gln Arg Gln
             180                 185                 190

Gln Leu Asp Tyr Gly Ile Tyr Val Ile Asn Gln Ala Gly Asp Thr Ile
             195                 200                 205

Phe Asn Arg Ala Lys Leu Leu Asn Val Gly Phe Gln Glu Ala Leu Lys
             210                 215                 220

Asp Tyr Asp Tyr Thr Cys Phe Val Phe Ser Asp Val Asp Leu Ile Pro
225                 230                 235                 240

Met Asn Asp His Asn Ala Tyr Arg Cys Phe Ser Gln Pro Arg His Ile
             245                 250                 255

Ser Val Ala Met Asp Lys Phe Gly Phe Ser Leu Pro Tyr Val Gln Tyr
             260                 265                 270

Phe Gly Gly Val Ser Ala Leu Ser Lys Gln Gln Phe Leu Thr Ile Asn
             275                 280                 285

Gly Phe Pro Asn Asn Tyr Trp Gly Trp Gly Gly Glu Asp Asp Asp Ile
             290                 295                 300

Phe Asn Arg Leu Val Phe Arg Gly Met Ser Ile Ser Arg Pro Asn Ala
305                 310                 315                 320

Val Val Gly Arg Cys Arg Met Ile Arg His Ser Arg Asp Lys Lys Asn
             325                 330                 335

Glu Pro Asn Pro Gln Arg Phe Asp Arg Ile Ala His Thr Lys Glu Thr
             340                 345                 350

Met Leu Ser Asp Gly Leu Asn Ser Leu Thr Tyr Gln Val Leu Asp Val
             355                 360                 365

Gln Arg Tyr Pro Leu Tyr Thr Gln Ile Thr Val Asp Ile Gly Thr Pro
             370                 375                 380

Ser
385
```

METHOD OF CO-EXPRESSING GALACTOSYLTRANSFERASE AND A GLYCOPROTEIN IN A TRANSGENIC PLANT CELL AND SIALYLATING THE GLYCOPROTEIN FOR PRODUCTION OF GLYCOPROTEIN HAVING HUMAN-TYPE SUGAR CHAIN

This application is a divisional of U.S. application Ser. No. 13/616,878 filed on Sep. 14, 2012, now allowed, which is a continuation of U.S. application Ser. No. 12/836,925, filed on Jul. 15, 2012, now U.S. Pat. No. 8,309,795, which is a continuation of U.S. application Ser. No. 11/717,956, filed Mar. 14, 2007, now abandoned, which is a continuation of U.S. application Ser. No. 10/466,941, filed on Jul. 18, 2003, now abandoned, which is a national stage filing under 35 U.S.C. 371 of international Application PCT/JP2002/00361, filed Jan. 18, 2002, which claims priority from Japanese Application No. 2001-12519, filed Jan. 19, 2001. The entire contents of each of the prior applications are incorporated by reference herein.

TECHNICAL FIELD

The present invention relates to a method for the secretory production of a heterologous glycoprotein having a human-type sugar chain using a plant cell, a plant cell capable of secreting this glycoprotein, and a glycoprotein having a human-type sugar chain secreted by this plant cell.

BACKGROUND ART

Production of extraneous proteins using plant cultured cells is proceeding. For example, attempts are being made to produce the following proteins useful for humans using tobacco cultured cell:

GM-CSF (see, E. A. James, C. Wang, Z., Wang, R. Reeves, J. H. Shin, N. S. Magnuson and J. M. Lee, "Production and Characterization of Biologically Active Human GM-CSF Secreted by Genetically Modified Plant Cells", Protein Expr. Purif., 19, 131-138 (2000)), IL-2 and IL-4 (ee, N. S. Magnuson, P. M. Linzmaier, R. Reeves, G. An, K. HayGlass and J. M. Lee, "Secretion of Biologically Active Human Interleukin-2 and Interleukin-4 from Genetically Modified Tobacco Cells in Suspension Culture", Protein Expr. Purif., 13, 45-52 (1998)), immunoglobulin (see, N. S. Magnuson, P. M. Linzmaier, J. W. Gao, R. Reeves, G. An and J. M. Lee, "Enhanced Recovery of a Secreted Mammalian Protein from Suspension Culture of Genetically Modified Tobacco Cells", Protein Expr. Purif 7, 220-228 (1996)), erythropoietin (see, S. Matsumoto, A. Ishii, K. Ikura, M. Ueda and R. Sasaki, "Expression of Human Erythropoietin in Cultured Tobacco Cells", Biosci. Biotechnol., Biochem., 57, 1249-1252 (1993)), and α1-antitrypsin (see, M. Terashima, Y. Mural, M. Kawamura, S. Nakanishi, T. Stoltz, L. Chen, W. Drohan, R. L. Rodriguez and S. Katoh, "Production of Functional Human al-Antitrypsin by Plant Cell Culture", Appl. Microbiol. Biotechnol., 52, 516-523 (1999)).

On other hand, it is reported that plant cultured cells secrete many proteins or glycoproteins (see, A. Sturm, "Heterogeneity of the Complex N-Linked Oligosaccharides at Specific Glycosylation Sites of Two Secreted Carrot Glycoproteins", Eur. J. Biochem., 199, 169-179 (1991); Y. Okushima, N. Koizumi, T. Kusano and H. Sano, "Secreted Proteins of Tobacco Cultured BY2 Cells: Identification of A New Member of Pathogenesis-Related Proteins", Plant Mol. Biol., 42, 479-488 (2000); and Y. Okushima, N. Koizumi, T. Kusano and H. Sano, "Glycosylation and Its Adequate Processing is Critical for Protein Secretion in Tobacco BY2 Cells", J. Plant Physiolo., 154, 623-627 (1999)). Of these, in the case of tobacco BY2 cultured cells, two kinds of peroxidases are purified and their genes have been cloned (see, H. Narita, Y. Asaka, K. Ikura; S. Matsumoto and R. Sasaki, "Isolation, Characterization and Expression of Cationic Peroxidase Isozymes Released into the Medium of Cultured Tobacco Cells", Eur. J. Biochem., 228, 855-862 (1995)). It is also reported that by adding polyvinylpyrrolidone (PVP) to the medium, the concentration of protein secreted in the medium could be increased (see, N. S. Magnuson, P. M. Linzmaier, J. W. Gao, R. Reeves, G. An and J. M. Lee, "Enhanced Recovery of A Secreted Mammalian Protein from Suspension Culture of Generically Modified Tobacco Cells", Protein Expr. Purif 7, 220-228 (1996)) and by Y. Okushima et al., supra. (1999) that from tobacco BY2 strain cultured cells, hundreds of proteins are extracellularly secreted. Among these, extracellular secretion of many glycoproteins are confirmed because of their reaction with lectin (concanavalin A) which recognizes high mannose-type sugar chains (see, Y. Okushima, supra. (1999)).

With respect to these glycoproteins, in particular, immunoglobulin, interleukin and GM-CSF, produced within plant cells, a signal peptide of each glycoprotein itself is also recognized in the secretion mechanism within the plant cell, and is secreted in the culture solution (see, E. A. James et al., supra.; N. S. Magnuson et al., supra. (1998); and N. S. Magnuson et al., supra. (1996)). In any of these glycoproteins, it is suggested, the sugar chain participates in the determination of half-life in blood, sensitivity to protease and stability. However, the sugar chain structures of recombinant proteins actually produced within plant cells and purified have not been examined and these proteins are presumed to have a plant-type sugar chain structure.

In the analysis of sugar chain structure, the secretion-type antibody molecule sIgA, produced from tobacco plants is revealed to have a plant-type sugar chain (see, M. Cabanes-Macheteau, A. C. Fitchette-Laine, C. Loutelier-Bourhis, C. Lange, N. D. Vine, J. K. Ma, P. Lerouge and L. Faye, "N-Glycosylation of a Mouse IgG Expressed in Transgenic Tobacco Plants", Glycobiology, 9, 365-372 (1999)). Furthermore, in the case where another antibody molecule is produced from the same tobacco plant body, the antibody protein produced within the cell is decomposed by the protease and is unstable (see, L. H. Stevens, G. M. Stoopen, I. J. Elbert, J. W. Molthoff, H. A. Bakker, A. Lommen, D. Bosch and W. Jordi, "Effect of Climate Conditions and Plant Developmental Stage on the Stability of Antibodies Expressed in Transgenic Tobacco", Plant Physiol., 124, 173-182 (2000)). By the Western method using an antiplant-type sugar chain antibody, addition of a plant-type sugar chain to this antibody is confirmed. Although it is reported that the β1,4-linked galactose residue present in the sugar chain of an antibody molecule produced by human or mouse contributes to the stabilization of antibody protein, this sugar residue is absent in the antibody molecule produced by plant cells. Because of this, the antibodies produced by tobacco plants are considered to be prone to decomposition by the protease.

In the case where erythropoietin is produced by tobacco cultured cells, the biological activity is recognized in vitro, but the activity in vivo is not detected (see, S. Matsumoto, K. Ikura, M. Ueda and R. Sasaki, "Characterization of a Human Glycoprotein (Erythropoietin) Produced in Cultured Tobacco Cells", Plant Mol. Biol., 27 1163-1172 (1995). This is concluded to occur because erythropoietin of which sugar chain is considered to greatly participate in the biological activity, has a largely different sugar chain structure when produced by plant cells.

On the other hand, it is suggested that the plant-type sugar chain may be an allergen in mammals including humans. That is, the sugar chain structure peculiar to plants, such as β1,2-xylose and α1,3-fucose which are not seen in glycoproteins of mammals, are reported to act as an allergen (see, K. Fotisch, F. Altmann, D. Haustein and S. Vieths, Involvement of Carbohydrate Epitopes in the IgE Response of Celery-Allergic Patients, Int. Arch. Allergy Immunol., 120, 30-42 (1999); I. B. Wilson, J. E. Harthill, N. P. Mullin, D. A. Ashford and F. Altmann, "Core α1,3-Fucose is a Key Part of the Epitope Recognized by Antibodies Reacting Against Plant N-Linked Oligosaccharides and is Present in a wide Variety of Plant Extracts", Glycobiology, 8, 651-661 (1998); and R. van Ree, M. Cabanes-Macheteau, J. Akkerdaas, J. P. Milazzo, C. Loutelier-Bourhis, C. Rayon, M. Villalba, S. Koppelman, R. Aalberse, R. Rodriguez, L. Faye and P. Lerouge, "β(1,2)-Xylose and α(1,3)-Fucose Residues Have a Strong Contribution in IgE Binding to Plant Glycoallergens", J. Biol. Chem., 275(15), 11451-11458 (Apr. 14, 2000). Accordingly, proteins for medical uses must have a sugar chain structure free of β1,2-xylose or α1,3-fucose.

DISCLOSURE OF THE INVENTION

The object of the present invention is to solve the above-described problems in conventional techniques and provide a method for the secretory production, in plant cells, of a glycoprotein which is stable, maintains its original physiological activity and is not an allergen, a plant cell capable of secreting such glycoprotein, and a glycoprotein having a human-type sugar chain secreted by this plant cell.

As a result of extensive investigations, the present inventors have found that when a human-derived galactose transferred enzyme gene cDNA is expressed in a tobacco cultured cell BY2 strain, galactose is added to sugar chains of most glycoproteins secreted to the exterior medium and the glycoproteins have a sugar chain structure free of β1,2-xylose or α1,3-fucose. The present invention has been accomplished based on this finding. Accordingly, when a human-derived useful protein is produced using this genetic recombinant tobacco cultured cell, the objective protein having a sugar structure which is not an allergen, can be secreted in the extracellular fluid.

The present invention relates to a method for the secretory production of a glycoprotein having a human-type sugar chain. This method comprises a step of introducing a gene of an enzyme capable of performing a transfer reaction of a galactose residue to a non-reducing terminal acetylglucosamine residue and a gene of a heterologous glycoprotein, into a plant, cell to obtain a transformed plant cell, and a step of culturing the obtained plant cell.

In the method above, the glycoprotein having a human-type sugar chain may comprise a core sugar chain and an outer sugar chain, the core sugar chain may substantially comprise a plurality of mannoses and acetylglucosamines, and the outer sugar chain may have a terminal sugar chain moiety containing a non-reducing terminal galactose.

In the method above, the outer sugar chain may have a linear or branched structure.

In the method above, the branched sugar chain moiety may be a mono-, bi-, tri- or tetra-structure In the method above, the glycoprotein may be free of fucose or xylose.

The method above for the secretory production may preferably further comprise a step of recovering the medium of the plant cells.

In one embodiment, the method above for the secretory production may further comprise a step of adding sugar or sugar chain in vitro.

In one aspect, the present invention relates to a plant cell which comprises a sugar chain-adding mechanism capable of performing a transfer reaction of a galactose residue to a non-reducing terminal acetylglucosamine residue and can secrete a protein with an added sugar chain added by the sugar chain-adding mechanism, wherein the sugar chain-adding mechanism adds a sugar chain comprising a core sugar chain and an outer sugar chain, the core sugar chain substantially comprises a plurality of mannoses and acetylglucosamines, and the outer sugar chain has a terminal sugar chain moiety containing a non-reducing terminal galactose.

The present invention further relates to a glycoprotein having a human-type sugar chain obtained by the method described above.

The present invention still further relates to a method for the secretory production of a glycoprotein having a human-type sugar chain, comprising a step of introducing a gene for an enzyme capable of performing a transfer reaction of a galactose residue to a non-reducing terminal acetylglucosamine residue and a gene for a heterologous glycoprotein, to obtain a transformed plant cell, and a step of expressing the enzyme within an intracellular organelle.

The present invention still further relates to a plant cell transformed with a gene for an enzyme capable of performing a transfer reaction of a galactose residue to a non-reducing terminal acetylglucosamine residue, wherein the enzyme is localized in the plant cell such that the plant cell is capable of synthesizing a glycoprotein having a human-type sugar chain structure.

In one aspect, in the plant cell above, the sugar chain structure includes an added galactose residue.

In one aspect, in the plant cell above, the sugar chain structure is free of β1,2-xylose or α1,3-fucose.

In one aspect, in the plant cell above, the sugar chain structure includes an galactose residue added to a N-linked type sugar chain of (N-acetylglucosamine)$_{1-2}$ (Mannose)$_{2-5}$ (N-acetylglucosamine)$_2$ selected from the group consisting of GlcNAc$_1$Man$_3$GlcNAc$_2$, GlcNAc$_1$Man$_5$GlcNAc$_2$, GlcNAc$_2$Man$_3$GlcNAc$_2$ and GlcNAc$_1$Man$_4$GlcNAc$_2$.

In one aspect, in the plant cell above, the enzyme is localized within an intracellular organelle in the plant cell.

The present invention still further relates to a plant regenerated from the plant cell above.

The present invention still further relates to a seed produced from the plant above.

BRIEF DESCRIPTION OF THE DRAWINGS

FIG. 3(A) shows the results when genomic DNA (40 μg) was digested by EcoRI and HindIII and then electrophoresed. The numerals in the left side show the sites of the DNA molecular weight marker. FIG. 3(B) shows a schematic view of fragment 2.2 kb containing promoter, hGT and terminator integrated into each transformant.

FIG. 4A is a view showing the analysis of PA-sugar chain prepared from GT6 strain culture medium by high-performance liquid chromatography.

BEST MODE FOR CARRYING OUT THE INVENTION

Figure 1:
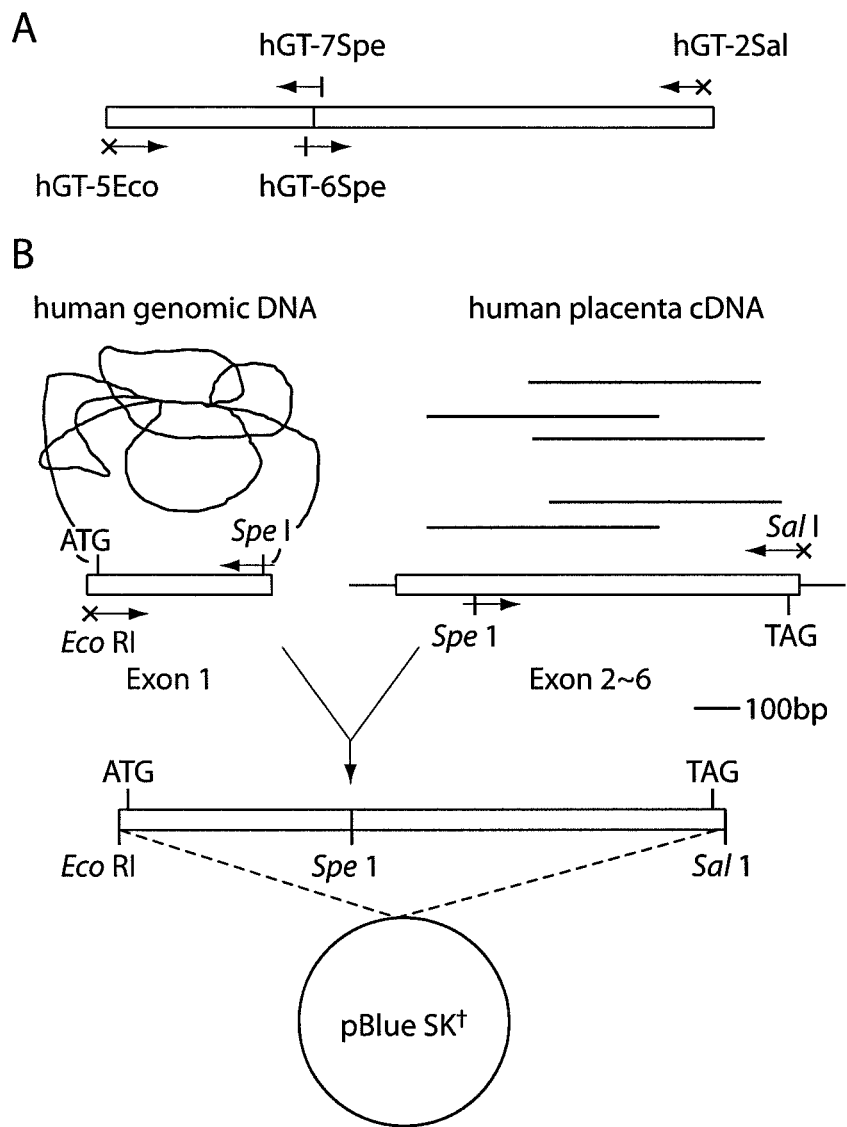
FIG. 1 is a schematic view showing a process for cloning hGT.

The present invention is described in detail below.

Herein, unless otherwise specified, protein separating and analyzing methods and immunological techniques known in the art can be employed. These techniques can be performed using commercially available kits, antibodies, marker substances and the like.

The method of the present invention is a method for producing a glycoprotein having a human type sugar chain. In the present invention, the "human-type sugar chain" means a sugar chain having a galactose residue bonded to an N-acetylglucosamine residue. The galactose residue in the human-type sugar chain may be a terminal of the sugar chain or a sialic acid residue may further be bonded to the outer side of the galactose residue. In the glycoprotein having a human-type sugar chain comprising a core sugar chain moiety, a branched sugar chain moiety and a terminal sugar chain moiety of the present invention, at least one of xylose and fucose is preferably not bonded in one or more of the moieties, more preferably in any of the moieties. Most preferably, the human-type sugar chain contains neither xylose nor fucose.

The plant cell may be any plant cell. The plant cell may have any form of cultured cell, cultured tissue, cultured organ and plant body. Among these, preferred are cultured cell, cultured tissue and cultured organ, more preferred is cultured cell. The plant species which can be used in the production method of the present invention may be any plant species which can perform the genetic transduction. Examples of the plant species which can be used in the production method of the present invention include plants belonging to Solanaceae, Gramlneae, Cruciferae, Rosaceae, Leguminosae, Cucurbitaceae, Labiatae, Liliaceae, Chenopodiaceae and Umbelliferae.

Examples of the Solanaceae plant include plants belonging to *Nicotiana, Solanum, Datura, Lynopersion* or *Petunia*, such as tobacco, egg-plant, potato, tomato, red pepper and *petunia*.

Examples of the Gramineae plant include plants belonging to *Oryza, Hordenum, Secaie, Sccaharum, Echinoohloa* or *Zea*, such as rice, barley, rye, barnyard millet, sorghum and corn.

Examples of the Cruciferae plant include plants belonging to *Raphanus, Brassica, Arabidopsis, Wasabia* or *Capseiia*, such as radish, rape, whitlowgrass, horseradish and shepherd's purse.

Examples of the Rosaceae plant include plants belonging to *Orunus, Aelus, Pynus, Fragaria* or *Rosa*, such as Japanese apricot, peach, apple, pear, strawberry and rose.

Examples of the Leguminosae plant include plants belonging to *Glycine, Vigna, Phaseolus, Pisan, Viola, Arachis, Trifolium, Alphalfa* or *Medicago*, such as soybean, red bean, kidney bean, green pea, horsebean, peanut, clover and bur clover.

Examples of the Cucurbitaceae plant include plants belonging to *Luffa, Cucurbita* or *Cucumis*, such as luffa, cushaw, cucumber and melon.

Examples of the Labiatae plant include plants belonging to *Lavandula, Mentha* or *Perilla*, such as lavender, mint and *perilla*.

Examples of the Liliaceae plant include plants belonging to *Allium, Lilium* or *Tulipa*, such as Welsh onion, garlic, lily and tulip.

Examples of the Chenopodiaceae plant include plants belonging to *Spinaoia*, such as spinach.

Examples of the Umbelliferae plant include plants belonging to *Angelica, Daucus, Cryptotaenia* or *Apitum*, such as *Angelica polyclada*, carrot, trefoil and celery.

Among these plants for use in the production method of the present invention, preferred are tobacco, tomato, potato, rice, corn, radish, soybean, green pea, bur clover and spinach, more preferred are tobacco, tomato, potato, corn and soybean.

The "enzyme capable of performing a transfer reaction of a galactose residue to a non-reducing terminal acetylglucosamine residue" means an enzyme which can transfer a galactose residue to a non-reducing terminal acetylglucosamine residue generated at the addition of a sugar chain after the synthesis of the protein moiety of a glycoprotein within a plant cell. Examples of such an enzyme include galactosyl transferase, lactose synthase and β-galactosidase. Such an enzyme may be derived from any animal species but is preferably derived from mammals, more preferably from human.

This enzyme is preferably localized in an intracellular organelle. Although restriction to a specific theory is not intended, the present inventors consider that this enzyme being present in an intracellular organelle, such as endoplasmic reticulum and Golgi body, thereby acting on a protein or sugar chain before a fucose or xylose residue is added, or acting so as to inhibit the addition of a fucose or xylose residue, at the time of expression and secretion of a heterologous glycoprotein in plant cells.

The "enzyme gene capable of performing a transfer reaction of a galactose residue to a non-reducing terminal acetylglucosamine residue" may be isolated from any animal cell using a nucleotide sequence known to code this enzyme, or a commercially available enzyme may be purchased or may be used after modifying it to suit to the expression in plants.

Herein, the "gene" means the structural gene moiety. In order to facilitate the expression in plants, a regulator sequence such as promoter, operator and terminator may be linked to the gene.

The "heterologous glycoprotein" means a glycoprotein which is originally not expressed in plants for use in the present invention. Examples of the heterologous glycoprotein include enzyme, hormone, cytokine, antibody, vaccine, receptor and serum protein. Examples of the enzyme include horseradish peroxidase, kinase, glucocerebrosidase, α-galactosidase, phytase, TPA (tissue-type plasminogen activator) and HMG-CoA reductase. Examples of the hormone and cytokine include enkephalin, interferon alpha, GM-CSF, G-CSF, chorionic gonadotropic hormone, interleukin-2, interferon beta, interferon gamma, erythropoietin, vascular endothelial growth factor, human chorionic gonadotropin (HCG), luteinizing hormone (LH), thyroid-simulating hormone (TSH), prolactin and follicle-stimulating hormone. Examples of the antibody include IgG, scFv and secretory IgA. Examples of the vaccine include hepatitis B surface antigen, rotavirus antigen, *Escherichia coli* enterotoxin, malaria antigen, G protein of rabies virus, and HIV virus glycoprotein (e.g., gp120). Examples of the receptor and matrix protein include EGF receptor, fibronectin, α1-antitrypsin and coagulation factor VIII. Examples of the serum protein include albumin, complement system protein, plasminogen, corticosteroid-binding globulin, Thyroxine-binding globulin and protein C.

The "gene of heterologous glycoprotein" may be isolated from any cell using a nucleotide sequence known to code the objective heterologous glycoprotein or a commercially available gene may be purchased or may be used after modifying it to suit to the expression in plants.

The gene of an enzyme capable of performing a transfer reaction of a galactose residue to a non-reducing terminal acetylglucosamine residue and the gene of heterologous glycoprotein are introduced into a plant cell by a method known in the art. These genes may be introduced separately or simultaneously. Those skilled in the art will appreciate that the choice of method might depend on the type of plant targeted for transformation.

Suitable methods of transforming plant cells include microinjection (Crossway et al., BioTechniques 4:320-334 (1986)), electroporation (Riggs et al., Proc. Natl. Acad. Sci. USA 83:5602-5606 (1986), *Agrobacterium*-mediated transformation (Hinchee et al., Biotechnology 6:915-921 (1988); See also, Ishida et al., Nature Biotechnology 14:745-750 (June 1996) for maize transformation), direct gene transfer (Paszkowski et al., EMBO J. 3:2717-2722 (1984); Hayashimoto et al., Plant Physiol 93:857-863 (1990)(rice)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6:923-926 (1988)). See also, Weissinger et al., Annual Rev. Genet. 22:421-477 (1988); Sanford et al., Particulate Science and Technology 5.27-37 91987)(onion); Svab et al., Proc. Natl. Acad. Sci. USA 87:8526-8530 (1990) (tobacco chloroplast); Christou et al., Plant Physiol. 87:671-674 (1988)(soybean); McCabe et al., Bio/Technology 6.923-926 (1988)(soybean); Klein et al., Proc. Natl. Acad. Sci. USA, 85:4305-4309 (1988)(maize); Klein et al., Bio/Technology 6:559-563 (1988) (maize); Klein et al., Plant Physiol. 91:440-444 (1988) (maize); Fromm et al., Bio/Technology 8:833-839 (1990); and Gordon-Kamm et al., Plant Cell 2: 603-618 (1990) (maize); Koziel et al., Biotechnology 11: 194-200 (1993) (maize); Shimamoto et al., Nature 338: 274-277 (1989) (rice); Christou et al., Biotechnology 9: 957-962 (1991) (rice); Datta et al., 131° 1/Technology 3:736-740 (1990) (rice); European Patent Application EP 0 332 581 (orchardgrass and other Pooideae); Vasil et al., Biotechnology 11: 1553-1558 (1993) (wheat); Weeks et al., Plant Physiol. 102: 1077-1084 (1993) (wheat); Wan et al., Plant Physiol. 104: 37-48 (1994) (barley); Jahne et al., Theor. Appl. Genet. 89:525-533 (1994) (barley); Umbeck at al., Bio/Technology 5: 263-266 (1987) (cotton); Casas et al., Proc. Natl. Acad. Sci. USA 90:11212-11216 (December 1993) (sorghum); Somers et al., Bio/Technology 10:1589-1594 (December 1992) (oat); Torbert et al., Plant Cell Reports 14:635-640 (1995) (oat); Weeks et al., Plant Physiol. 102:1077-1084 (1993) (wheat); Chang et al., WO 94/13822 (wheat) and Nehra et al., The Plant Journal 5:285-297 (1994) (wheat). A particularly preferred set of embodiments for the introduction of recombinant DNA molecules into maize by microprojectile bombardment can be found in Koziel et al., Biotechnology 11: 194-200 (1993), Hill et al., Euphytica 85:119-123 (1995) and Koziel et al., Annals of the New York Academy of Sciences 792:164-171 (1996). An additional preferred embodiment is the protoplast transformation method for maize as disclosed in EP 0 292 435. Transformation of plants can be undertaken with a single DNA species or multiple DNA species (i.e. co-transformation) and both these techniques are suitable for use with the peroxidase coding sequence.

The gene product expressed and secreted by the plant cell having incorporated thereinto the above-described genes can be identified by a method known in the art. Examples of the identification method include silver staining, Western blotting, Northern hybridization and detection of enzymatic activity.

The transformed cell expressing an enzyme capable of performing a transfer reaction of a galactose residue into a non-reducing terminal acetylglucosamine residue and expressing a heterologous glycoprotein, expresses and secretes a heterologous glycoprotein having a human-type sugar chain. In other words; the thus-obtained transformed plant has a human-type sugar chain-adding mechanism and by culturing this transformed cell, human-type glycoprotein can be expressed and secreted in a large amount in the medium.

This human-type glycoprotein comprises a core sugar chain and an outer sugar chain, and the core sugar chain substantially comprises a plurality of mannoses and acetylglucosamines. The outer sugar chain of the glycoprotein obtained contains a non-reducing terminal sugar chain moiety. The outer sugar chain may have a linear structure or a branched structure. The branched sugar chain moiety may be any of mono-, bi- tri- and tetra-structures. The glycoprotein produced by the transformed cell preferably is free of fucose or xylose.

The resulting transformed plant cell may be maintained in the state of cultured cell, may be differentiated into a specific tissue or organ, or may be regenerated in a complete plant body or in a part such as seed, fruit, leaf, root, stem or flower obtained from a complete plant body.

For the culture, differentiation or regeneration of the transformed plant cell, means and culture mediums known in the art are used. Examples of the medium include Murashige-Skoog (MS) medium, Gamborg B5 (B) medium, White medium and Nitsch & Nitsch (Nitsch) medium, however, the present invention is not limited thereto. These mediums are usually used after adding thereto an appropriate amount of a plant growth control substance (e.g., plant hormone) and the like.

Application of these systems to different plant strains depends upon the ability to regenerate that particular plant strain from protoplasts. Illustrative methods for the regeneration of cereals from protoplasts are described (Fujimura et al., Plant Tissue Culture Letters, 2:74, 1985; Toriyama et al., Theor. Appl. Genet., 73:16, 1986; Yamada et al., Plant Cell Rep., 4:85, 1986; Abdullah et al., Biotechnology, 4:1087, 1986).

To transform plant strains that cannot be successfully regenerated from protoplasts, other ways to introduce DNA into intact cells or tissues can be utilized. For example, regeneration of cereals from immature embryos or explants can be effected as described (Vasil, Biotechnology, 6:397, 1988).

*Agrobacterium*-mediated transfer is also a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described above.

Fundamentally, as long as the transformed plant cell grows and then expresses and secretes the desired gene product, a culture medium having any composition containing trace nutrients necessary for the growth of plant cells, such as carbon source, nitrogen source, vitamins and salts, may be used for the secretory production of a glycoprotein having a human-type sugar chain. Also, polyvinylpyrrolidone, protease inhibitor and the like may be added so as to stabilize the secreted heterologous protein and attain efficient secretion of the heterologous protein.

The glycoprotein having a human-type sugar chain expressed and secreted by the transformed plant cell can be typically isolated from the medium of plant cells. The isolation of glycoprotein from the medium of plant cells can be performed using a method well-known to one skilled in the art. For example, the glycoprotein can be purified to isolate it from the medium using, individually or in combination, techniques such as salting out (e. g., ammonium sulfate precipitation, sodium phosphate precipitation), solvent precipitation (e.g., protein fractional precipitation by acetone or ethanol), dialysis, gel filtration, ion exchange, column chromatography such as reverse phase, ultrafiltration, and high-performance chromatography (HPLC).

Alternatively, the glycoprotein of the present invention may also be isolated or extracted from plant cells. Furthermore, the glycoprotein of the present invention, which is contained in transformed cells, can be used as it is for food. The glycoprotein of the present invention has a human-type sugar chain addition and therefore, is free of antigenicity and suitable for the administration to animals including humans.

Further also included within the present invention, the plant cell or the plant body transformed with a gene of an enzyme capable of performing a transfer reaction of a galactose residue to a non-reducing terminal acetylglucosamine residue, may have inactivated or suppressed activity of $\beta 1,2$-xylose transfer enzyme or $\alpha 1,3$-fucose transfer enzyme.

Strasser et al. has isolated cDNA encoding $\beta 1,2$-xylosyltransferase from *Arabidopsis thaliana* (Strasser R, Mucha J, Mach L, Altmann F, Wilson I B, Glossl J, Steinkellner H, Molecular cloning and functional expression of $\beta 1,2$-xylosyltransferase cDNA from *Arabidopsis thaliana*. FEBS Lett. (2000) 472: 105-108). Homology searching against databases such as NIH GenBank may show nucleotide sequences corresponding to some EST (expression sequence tag) clones and genome sequence in some plants, are similar to the nucleotide sequence encoding *Arabidopsis* $\beta 1,2$-xylosyltransferase. Based on these sequences, nucleic acid encoding $\beta 1,2$-xylosyltransferase may be cloned from the host plant and used to establish a plant cell or plant with reduced xylosyltransferase activity by repressing β1,2-xylosyltransferase gene expression. Repression of β1,2-xylosyltransferase gene expression may be carried out by an antisense method, co-suppression method, RNAi method or so on.

Alternatively, a plant cell or plant with reduced xylosyltransferase activity may be established by chemical mutagenesis, site-directed mutagenesis using oligonucleotides, tagging methods or so on. In said plant, introduction and expression of one or more glycosyltransferase genes encoding galactose transferase together with a gene encoding a heterologous polypeptide may produce a heterologous polypeptide with humanized glycan structure or excrete a heterologous polypeptide with humanized glycan structure.

Similarly, Wilson et al. isolated cDNA encoding α 1,3-fucosyltransferase from *Arabidopsis thaliana* (Wilson I B, Rendic D, Freilinger A, Dumic J, Altmann F, Mucha J, Muller S, Hauser M T Cloning and expression of cDNAs encoding α1,3-fucosyltransferase homologues from *Arabidopsis thaliana*. Biochim Biophys Acta (2001) 1527:88-96). Leiter et al. isolated cDNA encoding α1,3-fucosyltransferase from mung bean (Leiter, H., Mucha, J., Staudacher, E., Grimm, R., Glossl, J., Altmann, F. Purification, cDNA cloning, and expression of GDP-L-Fuc:Asn-linked GlcNAc α1,3-fucosyltransferase from mung beans. J. Biol. Chem. (1999) 274:21830-21839). Homology searching against databases such as NIH GenBank may show nucleotide sequences corresponding to some EST (expression sequence tag) clones and genome sequence in some plants, are similar to the nucleotide sequence encoding *Arabidopsis* α1, 3-fucosyltransferase. Based on these sequences, nucleic acid encoding α1,3-fucosyltransferase may be cloned from the host plant and used to establish a plant cell or plant with reduced fucosyltransferase activity by repressing α1,3-fucosyltransferase gene expression. Repression of α1,3-fucosyltransferase gene expression can be carried out by an antisense method, co-suppression method, RNAi method or so on.

Alternatively, a plant cell or plant with reduced fucosyltransferase activity may be established by chemical mutagenesis, site-directed mutagenesis using oligonucleotides, tagging methods or so on. In said plant, introduction and expression of one or more glycosyltransferase genes encoding galactose transferase together with a gene encoding a heterologous polypeptide may produce a heterologous polypeptide with humanized glycan structure or excrete a heterologous polypeptide with humanized glycan structure.

EXAMPLES

The present invention is described below by referring to the Examples. The following Examples are only to illustrate but not to limit the present invention.

1. Cloning of Human β1-4 Galactose Transferase Gene

The β1-4 galactose transferase (hGt) (EC2.4.1.38) has been already cloned and a primary structure comprising 400 amino acids has been revealed (K. A. Masri et al., Biochem. Biophys. Res. Commun., 157, 657-663 (1988)).

(1) Primer Preparation and Template DNA

By referring to the report of Masri et al., the following primer were prepared.

```
hGT-5Eco:
                                        (SEQ. ID NO: 1)
5'-AAAGAATTCGCGATGCCAGGCGCGCGTCCCT-3'
```

```
hGT-2Sal:
                                        (SEQ. ID. NO: 2)
3'-TCGATCGCAAAACCATGTGCAGCTGATG-5' hGT-7Spe:
                                        (SEQ. ID. NO: 3)
3'-ACGGGACTCCTCAGGGGCGATGATCATAA-5' hGT6Spe:
                                        (SEQ. ID. NO: 4)
5'-AAGACTAGTGGGCCCCATGCTGATTGA-3'
```

As the template DNA, human genomic DNA, human placenta cDNA and human kidney cDNA purchased from Clontech were used.

(2) Cloning of hGT Gene cDNA

Using two combinations of (i) template of human genomic DNA with primers of hGT-5Eco and hGT-7Spe and (ii) template of human placenta cDNA with primers of hGT-2Sal and hGT6Spe, a PCR reaction was performed under the following conditions to obtain fragments of 0.4 kb and 0.8 kb containing an hGT-coding region.

(PCR Reaction System)

Water was added to 1 μl of template DNA, 5 μl of 10×PCR buffer, 4 μl of dNTPs (200 μM), primer (10 pmol) and 0.5 μl of Tag polymerase (produced by Takara Shuzo) (in the case of Tub polymerase, 0.2 μl) to make 50 μl.

(PCR Reaction Condition)

First Stage:
cycle number: 1, denaturation (94° C.): 5 min., annealing (55° C.): 1 min., extension (72° C.): 2 min. Second Stage:
cycle number: 30, denaturation (94° C.): 1 min., annealing (55° C.): 1 min., extension (72° C.): 2 min. Third Stage:
cycle number: 1, denaturation (94° C.): 1 min., annealing (55° C.): 2 min., extension (72° C.): 5 min.

Two fragments obtained were combined to construct hGT gene cDNA and subcloned into pBluescriptIISK+(SK). The pBluescriptIISK+(SK) was purchased from Stratagene. FIG. 1 shows the construction of plasmid containing hGT gene cDNA. SEQ. ID. NO:5 shows the base sequence of the obtained hGT gene and SEQ. ID. NO:6 shows the presumed amino acid sequence.

The obtained sequence was different from the hGT sequence disclosed in Masri et al. supra. in the following points: a) A at the position 528, C at the position 562 and A at the position 1047 were changed to G, T and G, respectively, but the amino acids coded were not changed; b) 9 bases at the positions 622 to 630 were deleted; and c) in order to connect the above-described fractions of 0.4 kb and 0.8 kb, G at the position 405 and T at the position 408 were transformed to A and A, respectively, at the preparation of primer.

Incidentally, the hGT gene cDNA which has two initiation codons (ATG), was designed in this experimentation such that the translation starts from the second initiation codon (position 37).

2. Introduction of hGT Gene into Tobacco Cultured Cell (1) hGT has been reported to be *Escherichia coli* expressed as an active type (see, D. Aoki et al., EMBO J., 9, 3171 (1990) and K. Nakazawa et al., J. Biochem., 113, 747 (1993)).

Figure 2:
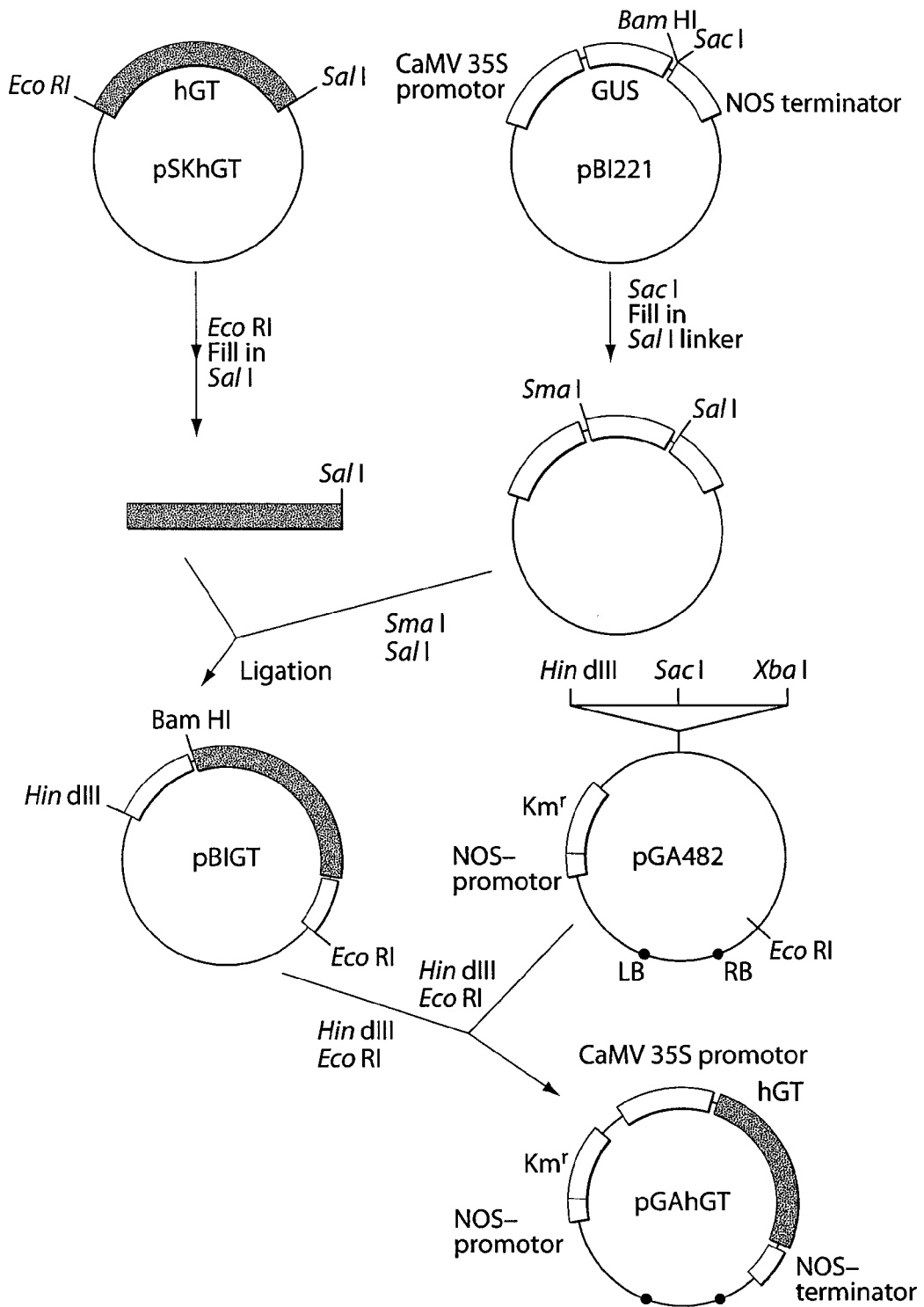
FIG. 2 is a schematic view showing a process for constructing vector pGAhGT for expressing hGT.

In order to express hGT in tobacco cultured cells, a vector pGAhGT for expression was constructed as shown in FIG. 2. The promoter used was cauliflower mosaic virus 35S promoter (CaMV 35S promoter) and the selectable marker used was kanamycin resistant gene. The pGAhGT was introduced into tobacco cultured cells through *Agrobacterium*.

The transformation of *Agrobacterium* was performed using a triparental mating method by Bevan et al (see, M. Bevan, Nucleic Acid Res., 12, 8711 (1984)). *Escherichia coli* DH 5α strain (suE44, ΔlacU169 (ψ80lacZAM15), hsdR17) (Bethesda Research Laboratories Inc., Focus 8(2), 9 (1986)) having pGA-type plasmid (see, G. An, Methods Enzymol. 153, 292 (1987)) and *Escherichia coli* HB101 having helper plasmid pRK2013 (see, M. Bevan, Nucleic Acid Res., 12, 8711 (1984)) each was cultured at 37° C. overnight in 2XYT medium containing 12.5 mg/L of tetracycline and 50 mg/L of kanamycin, and *Agrobacterium tumefaciens* EHA101 strain (see, E. H. Elizabeth, J. Bacteriol., 168, 1291 (1986)) was cultured at 28° C. over two nights in 2XYT medium containing 50 mg/L of kanamycin and 25 mg/L of chloramphenicol. From each culture medium, 1.5 ml was transferred into an EPPENDORF® tube and cells were collected and washed three times with LB medium. The obtained cells of each species were suspended in 100 μl of 2XYT medium, these three kinds of cells were mixed, the mixture was smeared on 2XYT agar medium and cultured at 28.degree. C. to conjugation-transmit the pGA-type plasmid from *Escherichia coli* to *Agrobacterium*. After 2 days, a part of cells grown throughout the surface of the 2XYT agar medium were scraped by a loop and coated on LB agar medium containing 50 mg/L of kanamycin, 12.5 mg/L of tetracycline and 25 mg/L of chloramphenicol. After culturing at 28° C. for 2 days, a single colony was selected.

The transformation of tobacco cultured cells was performed by the method described in G. An, Plant Mol. Bio. Manual, A3, 1. A suspension of *Agrobacterium* (EHA101 strain having pGA-type plasmid) cultured at 28° C. for 36 hours in LB medium containing 12.5 mg/L of tetracycline and a suspension of tobacco cultured cells (*Nicotiana tabacum* L. cv. bright yellow 2) after culturing for 4 days (purchased under Cell Name of BY-2 in catalogue No. RPC1 from The Institute of Physical and Chemical Research, Riken Gene Bank, Plant Cell Bank) were placed in a petri dish in amounts of 100 μl and 4 ml, respectively, then thoroughly mixed and left standing at 25° C. in a dark place. After 2 days, the culture medium in the petri dish was transferred into a centrifugation tube and the supernatant was removed by the centrifugal separation (1,000 rpm, 5 minutes). Subsequently, a fresh medium was added and after the centrifugal separation, the cells were smeared on a plate of modified LS agar medium containing from 150 to 200 mg/L of kanamycin and 250 mg/L of carbenicillin and left standing at 25° C. in the dark. After about 2 to 3 weeks, the callused cells were implanted on a new plate and the growing clones were selected. After further 2 to 3 weeks, the clones were transferred to 30 ml of modified LS medium having added thereto kanamycin and carbenicillin and subjected to passage culture. For about 1 month, the selection was repeated. From some resistant strains obtained, 6 resistant strains (GT1, 4, 5, 6, 8 and 9) were randomly selected.

(2) Identification of Introduced hGT Gene

The resistant strains obtained were analyzed by the Southern analysis and it was confirmed that the fragment of 2.2 kb containing CaMV35S promoter-hGT gene cDNA-NOS terminator in T-DNA was integrated into genomic DNA of tobacco cultured cell. From each resistant strain obtained above, genomic DNA was prepared, digested using EcoRI, HindIII, and analyzed by Southern analysis.

The preparation of chromosome DNA from tobacco cultured cells was performed according to the Watabe method (see, K. Watabe, "Cloning to Sequence (Cloning and Sequence)", Shokubutsu Biotechnology Jikken Manual (Plant Biotechnology Experimentation Manual), Noson Bunka Sha). 10 ml of Tobacco cultured cells were frozen by liquid nitrogen and ground into the powder form using mortar and pestle. Before liquefaction started, about 5 g of the thus-obtained powder was added to 5 ml of 2×CTAB (cetyltrimethylammonium bromide) solution preheated to 60° C. in a centrifugal tube (40 ml) and gradually well-mixed and while occasionally mixing at 60° C. for 10 minutes or more, the temperature was maintained. Thereto, 5 ml of chloroform:isoamyl alcohol (24:1) was added and thoroughly mixed until an emulsion was formed, and the emulsion was then centrifuged (2,800 rpm, 15 minutes, room temperature). The upper layer was transferred to a new 40 ml-volume centrifugal tube and the extraction operation using chloroform:isoamyl alcohol (24:1) was repeated. To the obtained upper layer, 1/10 volume of 10% CTAB was added and thoroughly mixed and centrifuged (2,800 rpm, 15 minutes, room temperature). The upper layer was transferred to a new centrifugal tube and 1 volume of cold isopropanol was added thereto, well mixed and centrifuged (4,500 rpm, 20 minutes, room temperature). After removing the supernatant by an aspirator, a TE buffer solution containing 5 ml of 1M sodium chloride was added and completely dissolved at 55 to 60° C. Thereto, 5 ml of cold isopropanol was added and when DNA was observed, the DNA was taken up using the end of a stick, transferred to an EPPENDORF® tube (containing 80% cold ethanol) and rinsed. The DNA was further rinsed with 70% ethanol and the dry precipitate was dissolved in an appropriate amount of TE buffer. Thereto, 5 μl of RNAaseA (10 mg/ml) was added and reacted at 37° C. for 1 hour. The 2×CTAB solution had a composition of 2% CTAB, 0.1M Tris-HCl (pH: 8.0), 1.4M sodium chloride and 1% polyvinyl pyrrolidone (PVP), and the 10% CTAB solution had a composition of 10% CTAB and 0.7M sodium chloride.

The Southern analysis was performed as follows.

(i) Electrophoresis and Alkali Modification of DNA:

After completely degrading 40 μg of the obtained chromosome DNA using a restriction enzyme, 1.5% agarose gel electrophoresis (50 V) was performed by a standard method. The gel was stained with ethidium bromide, photographed and shaken for 20 minutes in 400 ml of 0.25M HCl. Thereafter, the solution was discarded and the gel was immersed in 400 ml of modified solution (1.5M, NaCl, 0.5M, NaOH) and gradually shaken for 45 minutes. Subsequently, the solution was discarded and 400 ml of a neutralization solution (1.5M NaCl, 0.5M Tris-Cl (pH: 7.4)) was added and gradually shaken for 15 minutes. After discarding the solution, 400 ml of the neutralization solution was again added and gradually shaken for 15 minutes.

(ii) Transfer:

The DNA after the electrophoresis was transferred to a nylon membrane (HYBOND®-N Amersham) using 20×SSC. The transfer was performed for 12 hours or more. The blotted membrane was dried at room temperature for 1 hour and subjected to UV fixing for 5 minutes. The 20×SSC had a composition of 3M NaCl and 0.3M sodium citrate.

(iii) Preparation of DNA Probe

The DNA probe was prepared using Random prime Labeling Kit (produced by Takara Shuzo). In an EPPENDORF® tube, a reaction solution shown below was prepared and after heating at 95° C. for 3 minutes, rapidly cooled in ice: template DNA 25 ng, Random Primer 2 μl, water added to make 5 μl. 10× Buffer and dNTP each in 1.5 μl and [α-32P]dCTP (1.85 MBq, 50 mCi) in 5 μl were added, followed by filling up to 24 μl with H₂O. Thereto, 1 μl of Klenow fragment was added and after keeping at 37° C. for 10 minutes, eluted through NAP10 column (produced by Pharmacia) to purify the DNA. This purified DNA was heated at 95° C. for 3 minutes and then rapidly cooled in ice to obtain a hybridization probe.

(iv) Hybridization:

To the following prehybridization solution, 0.05 mg/ml of 0.5% (w/v) SDS was added. In the resulting solution, the membrane of (ii) above was immersed and the prehybridization was performed at 42° C. for 2 hours or more. Thereafter, the DNA probe prepared in (iii) was added and the hybridization was performed at 42° C. for 12 hours or more. The prehybridization solution had a composition of 5×SSC. 50 mM sodium phosphate, 50% (w/v) formamide, 5×Denhardt's solution (obtained by diluting 100×Denhardt's solution), 0.1% (w/v) SDS. The 100×Denhardt's solution had a composition of 2% (w/v) BSA, 2% (w/v) Ficol 400, 2% (w/v) polyvinyl pyrrolidone (PVP).

(v) Autoradiography:

After the cleaning in the following sequence, the autoradiography was performed by a standard method. Twice in 2×SSC and 0.1% SDS at 65° C. for 15 minutes and then, once in 0.1×SSC and 0.1% SDS at 65° C. for 15 minutes.

Figure 3:
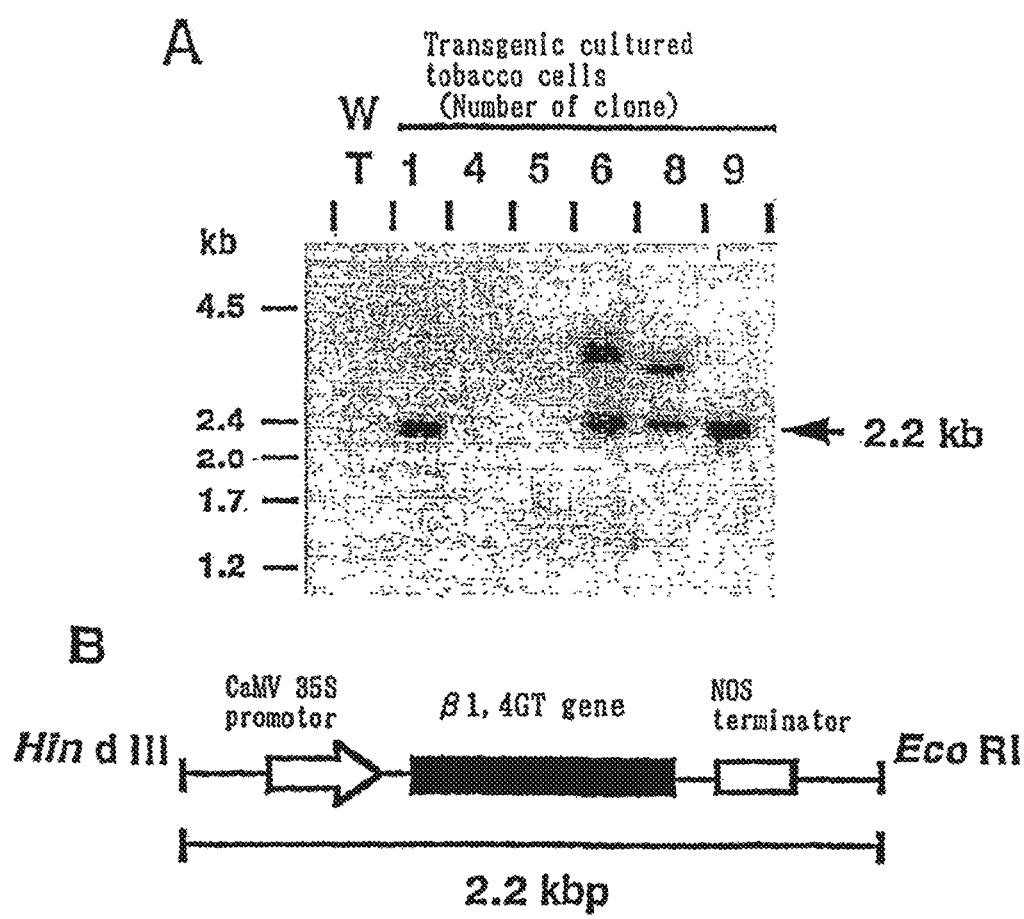
FIG. 3 is a photograph showing the Southern analysis of genome of transformant tobacco cultured cell.

FIG. 3 shows the results of the Southern analysis of genomic DNA prepared each resistant strain obtained above. As seen from FIG. 3, it was confirmed that the hGT gene was integrated in four strains of GT1, 6, 8 and 9.

3. Analysis of Glycoprotein Secreted by Galactosyl Transferase Transformant (Preparation of Glycoprotein by Extracellular Secretion of Tobacco Cultured Cell GT6 Strain)

A culture medium of tobacco cultured cell GT6 strain resulting from culturing in modified Murashige-Skoog medium prepared using mixed salts for Murashige-Skoog medium (produced by Wako Junyaku) for 7 days was centrifuged at 2,000 rpm for 10 minutes at room temperature and the obtained supernatant was recovered as the GT6 strain culture medium and used in this Example. The obtained supernatant was dialyzed against dH₂O (deionized water) (1×10⁵ times dilution) and then freeze-dried.

(Preparation of N-Linked Type Sugar Chain)

The sample obtained by the freeze-drying was hydrazinolyzed at 100° C. for 10 hours to excise the sugar chain. To the hydrazinolysis product, excess acetone was added and by centrifugation at 4° C. and 10,000 rpm for 20 minutes, sugar chains were precipitated. The sugar chains were N-acetylated in the presence of an aqueous saturated sodium hydrogencarbonate solution and acetic anhydride, then desalted using. DOWEX® 50X2 (produced by Muromachi Kagaku Kogyo), and passed through SEPHADEX® G-25 superfine gel filter column (1.8×180 cm) equilibrated with 0.1N aqueous ammonia, thereby recovering the N-linked sugar chains.

(Preparation of Pyridylaminated (PA) Sugar Chain)

The recovered N-linked sugar chains were PA-formed. The PA-sample was passed through Sephadex G-25 super fine gel filter column (1.8×180 cm) equilibrated with an aqueous 3% acetic acid solution to purify the PA-sugar chains.

(Fractionation and Analysis of PA-Sugar Chains by HPLC)

The PA-sugar chain structure was analyzed by reversed-phase (RP) and size-fractionation (SF) HPLC, two-dimensional sugar chain mapping using the exoglycosidase digestion, and IS-MS/MS analysis. In the HPLC (high-performance liquid chromatography) analysis. Jasco 880-PU HPLC having Jasco 821-FP Intelligent Spectrofluorometer was used and the fluorescence intensity was measured at excitation wavelength of 310 nm and fluorescence wavelength of 380 nm.

In the RP-HPLC analysis using COSMOSIL® 5C18-P column (6×250 mm, produced by Nakaraitesc), the concentration of acetonitrile in an aqueous 0.02% TFA solution was increased from 0% to 6% over 40 minutes at a flow rate of 1.2 ml/min and thereby PA-sugar chains were eluted. In the SF-HPLC analysis using ASAHIPAK® NH2P-50 column (4.6×250 mm, produced by Showa Denko K.K.), the concentration of acetonitrile in a dH₂O-acetonitrile mixed solution was increased from 26% to 50% over 25 minutes at a flow rate of 0.7 ml/min and thereby PA-Sugar chains were eluted.

(Analysis of PA-Sugar Chains by Exoglycosidase Digestion)

In the enzymatic digestion reaction using β-galactosidase (*Diplococcus pneumoniae*, Roche), each β-sugar chain was reacted at 37° C. for 2 days in a 0.1M sodium acetate buffer (pH: 5.5) containing 5 mU of β-galactosidase. Similarly, in the enzymatic digestion reaction using N-acetylglucosamidase (*Diplococcus pneumoniae*, Roche), each PA-sugar chain was reacted at 37° C. for 2 days in a 0.1M sodium acetate buffer (pH: 5.5) containing 5 mU of N-acetylglucosamidase. Furthermore, in the enzymatic digestion reaction using α-mannosidase (Jack bean, Sigma), each PA-sugar chain was reacted at 37° C. for 2 days in a 0.1M sodium acetate buffer (pH: 3.88) containing 10 mM zinc acetate and 10 RU of α-mannosidase. Each enzymatic digestion reaction was stopped by boiling the solution at 100° C. for 3 minutes. Then, the reaction solution was centrifuged at 12,000 rpm for 10 minutes and the supernatant was subjected to HPLC. The elution time of each sample sugar chain was compared with the elution time of a known sugar chain.

(IS-MS/MS Analysis)

The IS-MS/MS Analysis was performed using Perkin-Elmer SCIEX® API-III triple-quadrupole mass spectrometer. The scan interval was 0.5 Da.

(Sialic Acid Transferase Reaction In Vitro)

The GT6 strain cell culture medium-derived glycoprotein prepared above after the dialysis and freeze-drying was used as the substrate. A sialic acid transferase reaction was performed at 37° C. for 5 hours in 62.5 mM sodium cacodylate buffer solution (pH: 6.0) containing 1 mg/ml of BSA, 0.5% of Triton CF-54, 2 μM of CMP-sialic acid, 6 mU of α2,6-sialyl transferase (derived from rat liver) (produced by Wako Junyaku) and 400 μg of GT6 strain cell culture medium-derived glycoprotein. In the control test, 400 μg of BY2 strain cell culture medium-derived glycoprotein and 40 μg of asialo fetuin fetal (fetal bovine serum, Sigma) were used as the substrate.

(Lectin Staining)

The sialic acid transferase reaction product was subjected to SDS-PAGE at 130 V for 2 hours using 12.5% polyacrylamide gel and then transferred to nitrocellulose membrane at a constant current of 1 mA/cm² for 50 minutes. In the lectin blotting, horseradish peroxidase-linked SNA lectin (produced by EY Laboratories, Inc.) 200-fold diluted with a PBS solution containing 0.05% of Tween-20 was used. After the blotting, the staining was performed using POD Immunostain Kit (produced by Wako Junyaku).

(Purification of Tobacco Cultured Cell GT6 Strain Culture Medium-Derived PA-Sugar Chain)

Figure 4B:
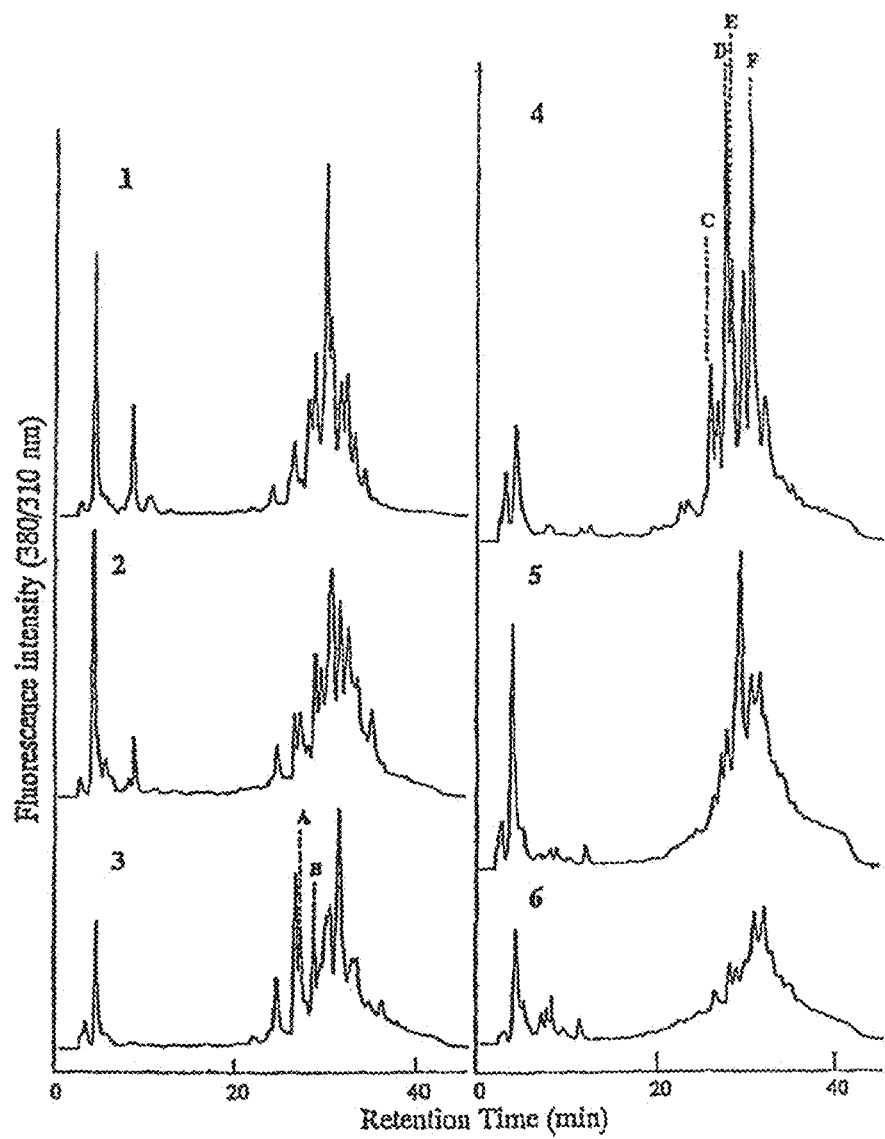
FIG. 4B is a view showing the analysis of PA-sugar chain prepared from GT6 strain culture medium by high-performance liquid chromatography.

The PA-sugar chain prepared from the GT6 strain culture medium was purified using RP-HPLC and SF-HPLC (shown in FIG. 4A and FIG. 4B, respectively). FIG. 4A shows the peak of PA-product by RP-HPLC. After the recovery of peaks (1 to 6), each was subjected to SF-HPLC (see, FIG. 4B).

Figure 5:
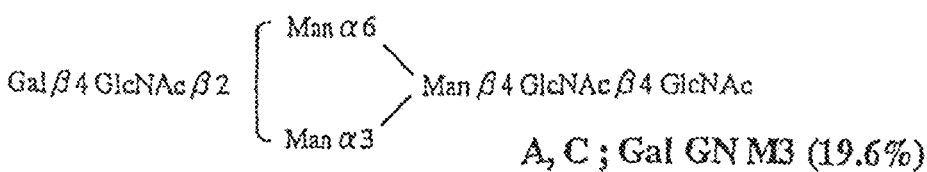
FIG. 5 is a view showing the structures and analysis results of sugar chains in the glycoprotein secreted in the GT6 strain culture medium. The numerals in parentheses in the Figure show the molar ratio of sugar chain having each structure shown in the Figure.
Figure 5:
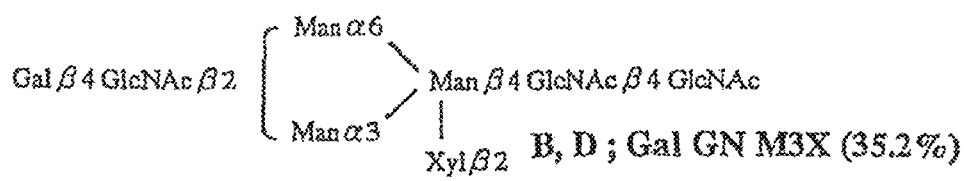
Figure 5:
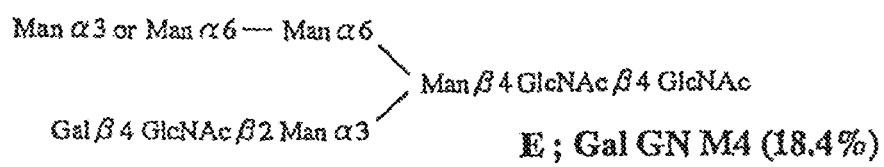
Figure 5:
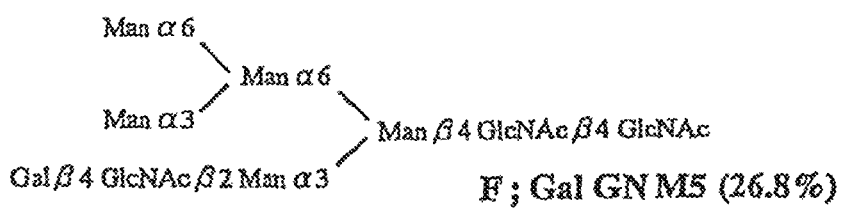

Exclusive of 6 peaks (shown by A to F in FIG. 4B) obtained by the SF-HPLC, the peaks were not an N-linked sugar chain. This was verified because, in IS-MS/MS analysis, signals agreeing with m/z 299.33 (GlcNAc-PA) and m/z 502.52 (GlcNAc$_2$-PA) were not obtained. FIG. 5 shows N-linked sugar chain structures analyzed on the peaks (A-F). In FIG. 5, the numerals in parentheses indicate the molar ratio of sugar chain having each structure shown in the Figure.

As shown in FIG. 5, A to F are all a human-type sugar chain having a galactose residue bound to an N-acetylglucosamine residue, contain no fucose residue and except for B and D, have no xylose residue.

(Structural Analysis of Tobacco Cultured Cell GT6 Culture Medium-Derived PA-Sugar Chain)

The molecular weight (m/z 1354.8) obtained by the IS-MS analysis of the peak A (I in FIG. 6) agreed with GalGlcNAcMan$_3$GlcNAc$_2$-PA (1354.27). The signals obtained by the IS-MS/MS analysis, namely, m/z 1192.5, m/z 990.5, m/z 827.5, m/z 665.5, m/z 503.0, m/z 300.0, are presumed to be GlcNAcMan$_3$GlcNAc$_2$-PA (1192.13) Man$_3$GlcNAc$_2$-PA (988.94), Man$_2$GlcNAc$_2$-PA (826.80), ManGlcNAc$_2$-PA (664.66), GlcNAc$_2$-PA (502.52) and GlcNAc-PA (299.33), respectively, and this suggests that the peak A contains these structures (the data are not shown).

Figure 6:
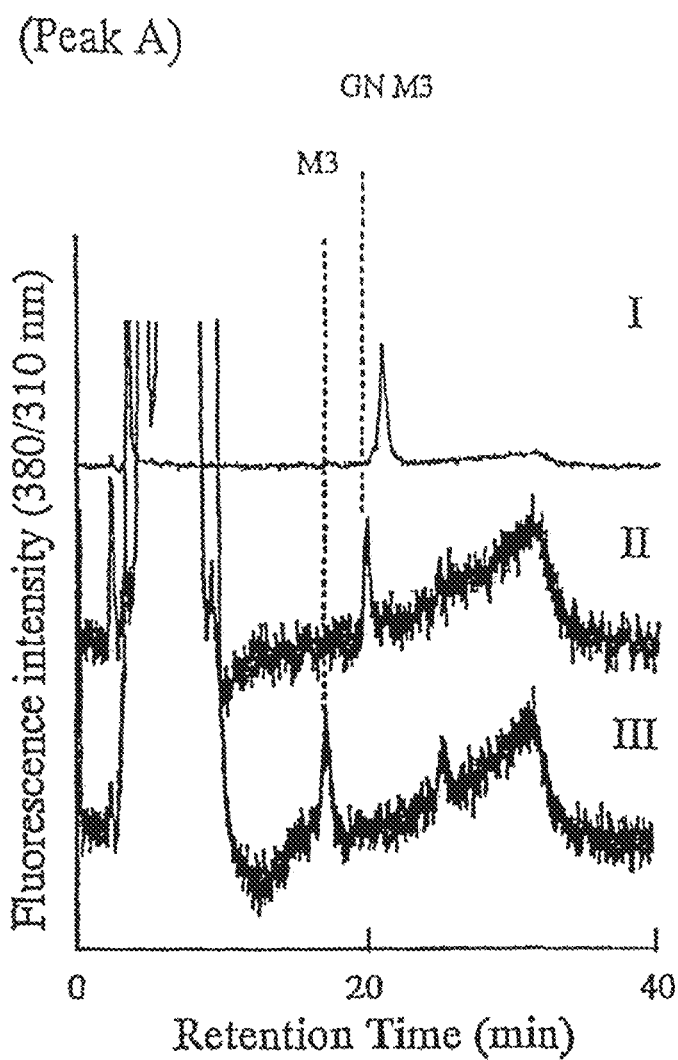
FIG. 6 is a view showing the analysis of PA-sugar chain prepared from GT6 strain culture medium and the exoglycosidase digestion product thereof by high-performance liquid chromatography.

The f-galactosidase digestion product from the peak A was GlcNAcMan$_3$GlcNAc$_2$-PA (II in FIG. 6) and the N-acetylglucosaminidase digestion product thereof was Man$_3$GlcNAc$_2$-PA (III in FIG. 6).

The molecular weight (m/z 1486.8) obtained by the IS-MS analysis of the peak B (I in FIG. 7) agreed with GalGlcNAcMan$_3$XylGlcNAc$_2$-PA (1486.38). The signals obtained by the IS-MS/MS analysis, namely, m/z 1354.5, m/z 1324.0, m/z 1324.0, m/z 1122.0, m/z 991.5. m/z 960.0, m/z 666.0, m/z 503.0 and m/z 300.0, are presumed to be GalGlcNAcMan$_3$GlcNAc$_2$-PA (1354.27), GlcNAcMan$_3$XylGlcNAc$_2$-PA (1324.24), Man$_3$XylGlcNAc$_2$-PA (1121.05), Man$_3$GlcNAc$_2$-PA (988.94), Man$_2$XylGlcNAc$_2$-PA (958.91), ManGlcNAc$_2$-PA (664.66), GlcNAC$_2$-PA (502.52) and GlcNAc$_2$-PA (299.33), respectively, and this suggests that the peak B contains these structures (the data are not shown).

Figure 7:
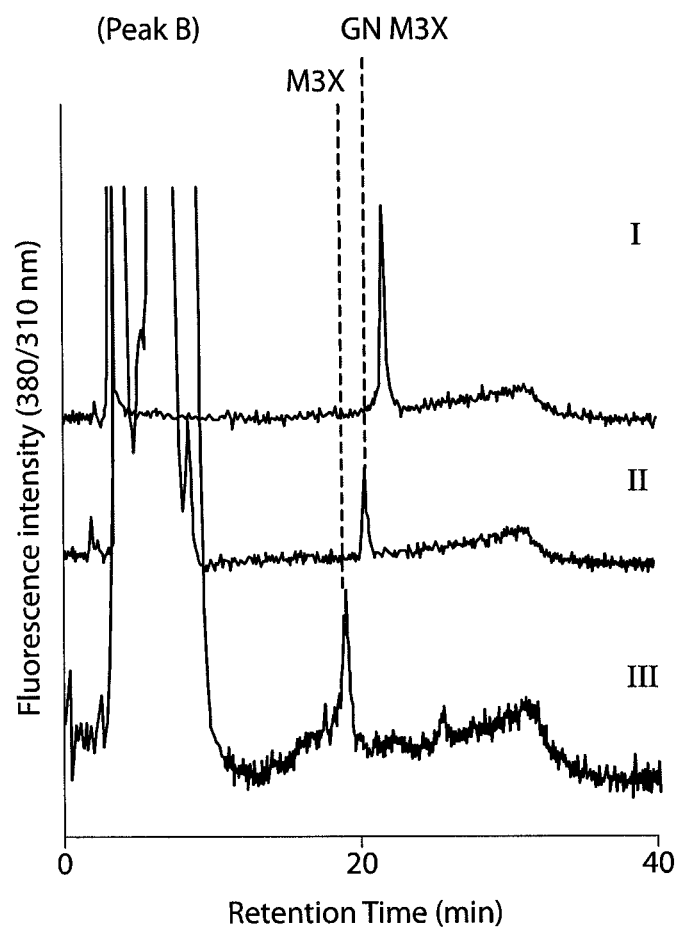
FIG. 7 is a view showing the analysis of PA-sugar chain prepared from GT6 strain culture medium and the exoglycosidase digestion product thereof by high-performance liquid chromatography.

The β-galactosidase digestion product from the peak B was GlcNAcMan$_3$XylGlcNAc$_2$-PA (II in FIG. 7) and the N-acetylglucosaminidase digestion product thereof was Man$_3$XylGlcNAc$_2$-PA (III in FIG. 7).

The molecular weight (m/z 1355.0) obtained by the IS-MS analysis of the peak C (I in FIG. 8) agreed with GalGlcNAcMan$_3$GlcNAc$_2$-PA (m/z 1354.27), The signals obtained by the IS-MS/MS analysis, namely, m/z 1193.5, m/z 989.0. m/z 827.0, m/z 665.5, m/z 503.0, m/z 300.0, are presumed to be GlcNAcMan$_3$GlcNAc$_2$-PA (m/z 1192.13), Man$_3$GlcNAc$_2$-PA (m/z 988.94), Man$_2$GlcNAc$_2$-PA (m/z 826.80). ManGlcNAc$_2$-PA (m/z 664.66), GlcNAc$_2$-PA (m/z 502.52) and GlcNAc-PA (m/z 299.33), respectively, and this suggests that the peak C contains these structures (the data are not shown).

Figure 8:
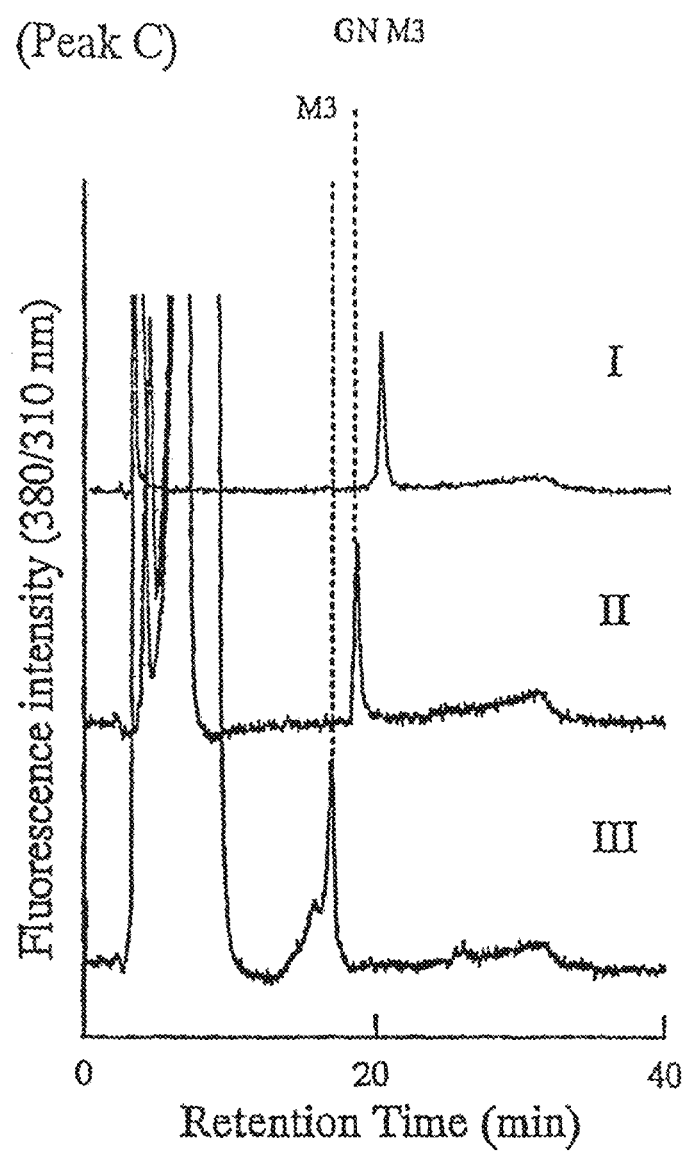
FIG. 8 is a view showing the analysis of PA-sugar chain prepared from GT6 strain culture medium and the exoglycosidase digestion product thereof by high-performance liquid chromatography.

The β-galactosidase digestion product from the peak C was GlcNAcMan$_3$GlcNAc$_2$-PA (II in FIG. 8) and the N-acetylglucosaminidase digestion product thereof was Man$_3$GlcNAc$_2$-PA (III in FIG. 8).

The molecular weight (m/z 1487.0, A in FIG. 10) obtained by the IS-MS analysis of the peak D (I in FIG. 9) agreed with GalGlcNAcMan$_3$XylGlcNAc$_2$-PA (m/z 1486.38). The signals obtained by the IS-MS/MS analysis, namely, m/z 1354.0, m/z 1325.0, m/z 1191.0, m/z 1121.5, m/z 989.5, m/z 828.5, m/z 503.0 and m/z 300.5, are presumed to be GalGlcNAcMan$_3$GlcNAc$_2$-PA (m/z 1354.27), GlcNAcMan$_3$XylGlcNAc$_2$-PA (m/z 1324.24), GlcNAcMan$_3$GlcNAc$_2$-(m/z 1192.13), Man$_3$XylGlcNAc$_2$-PA (m/z 1121.05), Man$_3$GlcNAc$_2$-PA (m/z 988.94), Man$_2$GlcNAc$_2$-PA (m/z 826.80), GlcNAc$_2$-PA (m/z 502.52) and GlcNAc-PA (m/z 299.33), respectively, and this suggests that the peak D contains these structures (B in FIG. 10).

Figure 9:
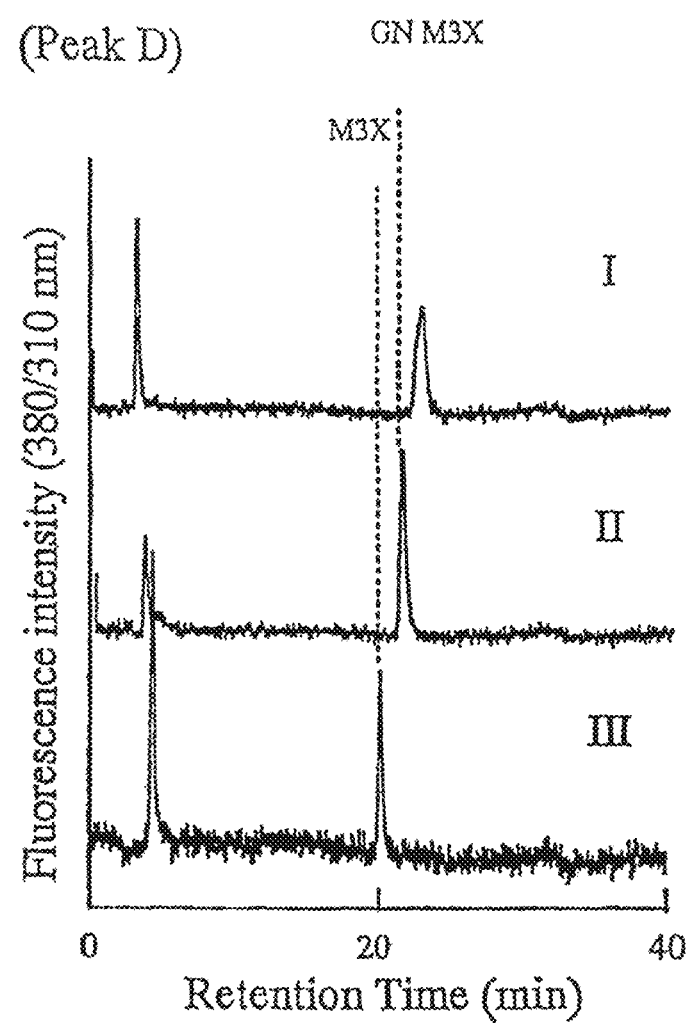
FIG. 9 is a view showing the analysis of PA-sugar chain prepared from GT6 strain culture medium and the exoglycosidase digestion product thereof by high-performance liquid chromatography.
Figure 10:
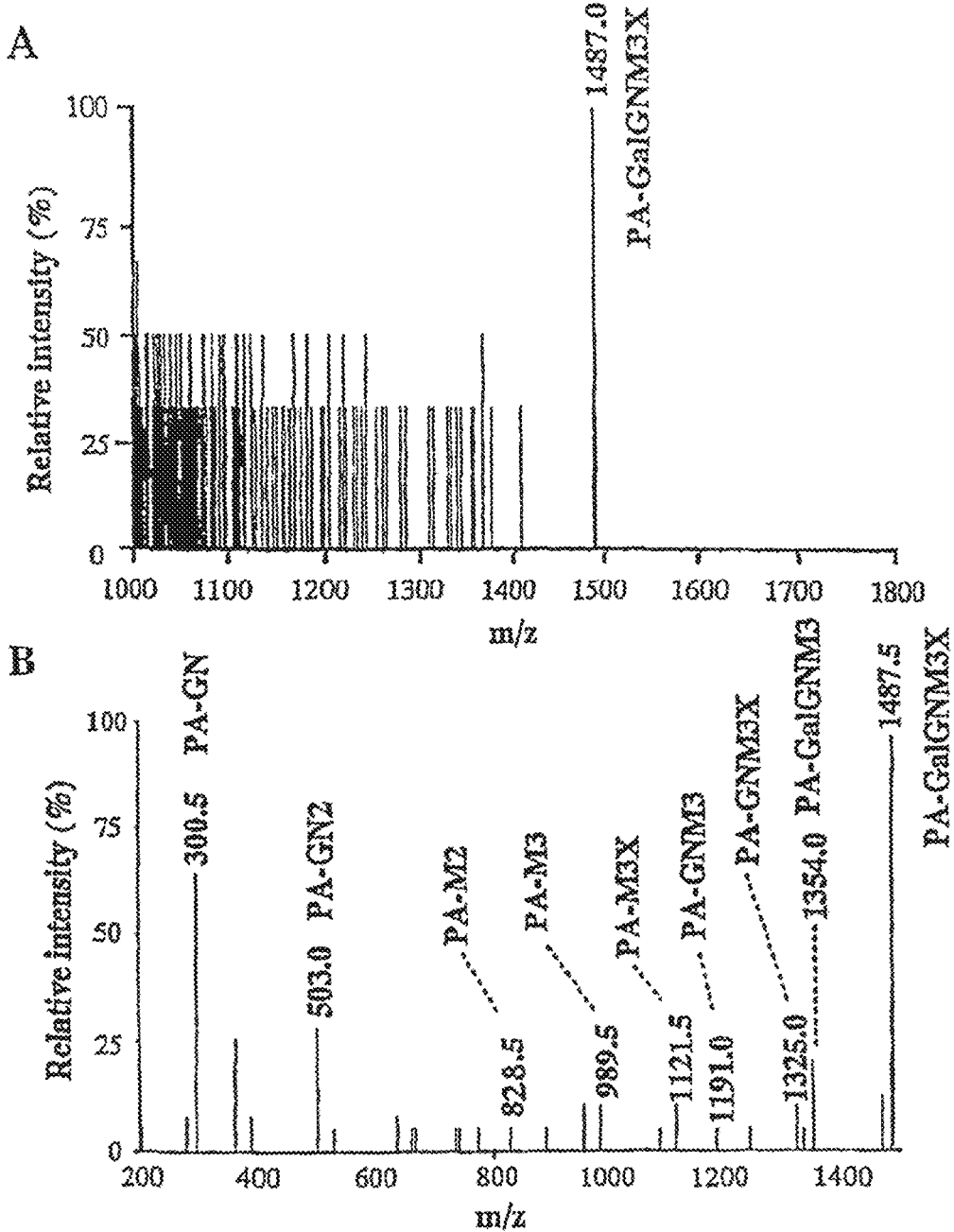
FIG. 10 is a view showing the IS-MS/MS analysis of PA-sugar chain prepared from GT6 strain culture medium. B is a partial enlarged view of A.

The β-galactosidase digestion product from the peak D was GlcNAcMan$_3$XylGlcNAc$_2$-PA (II in FIG. 9) and the N-acetylglucosaminidase digestion product thereof was Man$_3$XylGlcNAc$_2$-PA (III in FIG. 9).

The molecular weight (m/z 1516.6) obtained by the IS-MS analysis of the peak E (I in FIG. 11) agreed with GalGlcNAcMan$_4$GlcNAc$_2$-PA (1516.41). The signals obtained by the IS-MS/MS analysis, namely, m/z 1355.0, m/z 1193.0, m/z 990.0, m/z 826.5, m/z 665.0, m/z 503.5 and m/z 300.0, are presumed to be GalGlcNAcMan$_3$GlcNAc$_2$-PA (m/z 1354.27), GalNAcMan$_3$GlcNAc$_2$-PA (m/z 1192.13), Man$_3$GlcNAc$_2$-PA (m/z 988.94), Man$_2$GlcNAc$_2$-PA (m/z 826.80), ManGlcNAc$_2$-PA (m/z 664.66) GlcNAc$_2$-PA (m/z 502.52) and GlcNAc-PA (m/z 299.33), respectively, and this suggests that the peak E contains these structures (the data are not shown).

Figure 11:
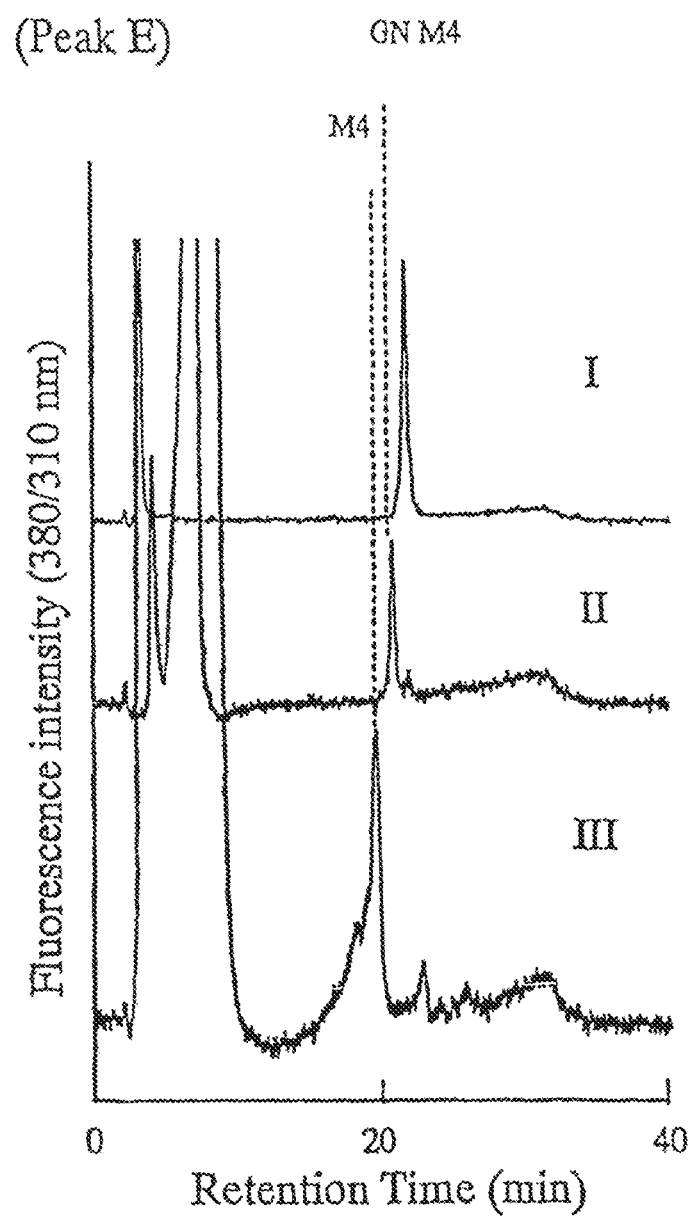
FIG. 11 is a view showing the analysis of PA-sugar chain prepared from GT6 strain culture medium and the exoglycosidase digestion product thereof by high-performance liquid chromatography.

The β-galactosidase digestion product from the peak E was GlcNAcMan$_4$GlcNAc$_2$-PA (II in FIG. 11) and the N-acetylglucosaminidase digestion product thereof was Man$_4$GlcNAc$_2$-PA (III in FIG. 11).

The molecular weight (m/z 1679.8) obtained by the IS-MS analysis of the peak F (I in FIG. 12) agreed with GalGlcNAcMan$_5$GlcNAc$_2$-PA (1678.55). The signals obtained by the IS-MS/MS analysis, namely, m/z 1517.5, m/z 1313.5, m/z 1152.0, m/z 827.5, m/z 665.5, m/z 503.0 and m/z 300.0, are presumed to be GlcNAcMan$_3$GlcNAc$_2$-PA (m/z 1516.41). Man$_9$GlcNAc$_2$-PA (1313.22), Man$_4$GlcNAc$_2$-PA (1151.08), Man$_2$GlcNAc$_2$-PA (826.80), ManGlcNAc$_2$-PA (664.66), GlcNAc$_2$-PA (502.52) and GlcNAc-PA (m/z 299.33), respectively, and this suggests that the peak F contains these structures (the data are not shown).

Figure 12:
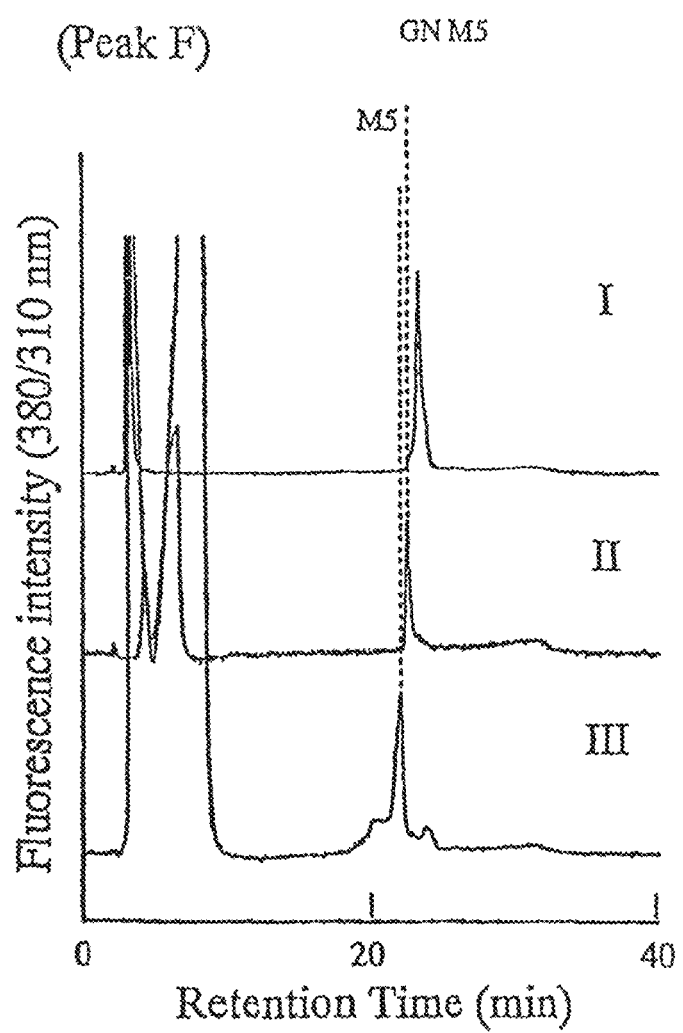
FIG. 12 is a view showing the analysis of PA-sugar chain prepared from GT6 strain culture medium and the exoglycosidase digestion product thereof by high-performance liquid chromatography.

The β-galactosidase digestion product from the peak F was GlcNAcMan$_5$GlcNAc$_2$-PA (II in FIG. 12) and the N-acetylglucosaminidase digestion product thereof was Man$_5$GlcNAc$_2$-PA (III in FIG. 12).

From these results, the peak A or C is considered to be either α-D-Man-(1→6) [β-D-Gal-(1→4)-β-D-GlcNAc-(1→2)-α-D-Man-(1→3)] β-D-Man-(1→4)-β-D-GlcNAc-(1-44)-GlcNAc-PA(GalGN$_1$M3-PA) or [β-D-Gal-(1→4)-β-D-GlcNAc(1→2)-α-D-Man-(1→6)] α-D-Man-(1→3) β-D-Man-(1→4)-β-D-GlcNAc-(1→4)-GlcNAc-PA (GalGN$^1$M3-PA).

The peak B or D is considered to be either α-D-Man-(1→6) [β-D-Gal-(1→4)-β-D-GlcNAc-(1→2)-α-D-Man-(1→3)] [β-D-Xyl-(1→2)] β-D-Man-(1→4)-β-D-GlcNAc-(1→4)-GlcNAc-PA (GalGN$_1$M3X-PA) or [β-D-Gal-(1-4)-β-D-GlcNaC-(1→2)-α-D-Man-(1→6)] [α-D-Man-(1→3)] [β-D-Xyl-(1→2)] β-D-Man-(1→4)-β-D-GlcNAc-(1→4)-GlcNAc-PA (GalGN$^1$M3X-PA).

The peak E is considered to be either α-D-Man-(1→6)-α-D-Man-(1→6) [β-D-Gal-(1→4)-β-D-GlcNAc-(1→2)-α-D-Man-(1→3)]β-D-Man-(1→4)β-D-GlcNAc-(1→4)-GlcNAc-PA (GalGNM4-PA) or α-D-Man-(1→3)-α-D-Man- (1→6) [β-D-Gal-(1→4)-β-D-GlcNAc(1→2)-α-D-Man-(1→3)] β-D-Man-(1→4)-β-D-GlcNAc-(1→4)-GlcNAc-PA (GalGNM4-PA).

The peak F is considered to be α-D-Man-(1→6) [α-D-Man-(1→3)] α-D-Man-(1→6) [β-D-Gal-(1→4)-β-D-GlcNAc(1→2)-α-D-Man-(1→3)] β-D-Man-(1→4)-β-D-GlcNAc-(1→4)-GlcNAc-PA (GalGNM5-PA).

(Sialic Acid Transferase Reaction In Vitro)

Figure 13:
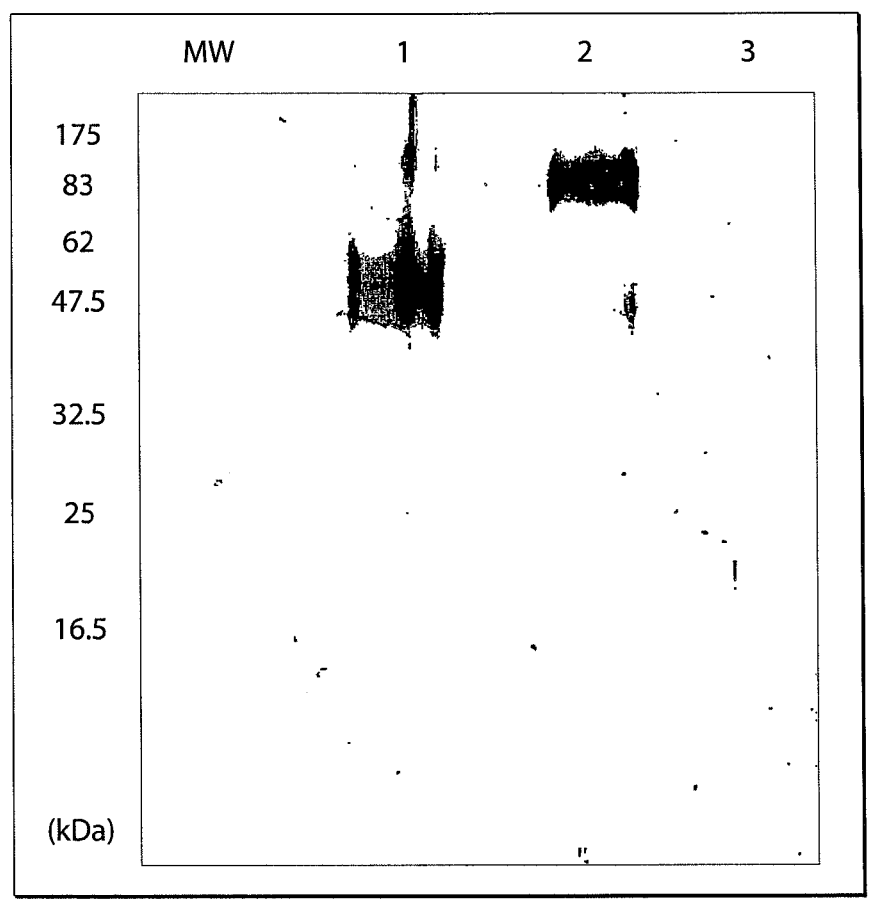
FIG. 13 is a photograph showing the results of sialic acid transferase reaction in vitro using GT6 stain culture medium-derived glycoprotein, BY2 strain culture medium-derived glycoprotein or asialo fetuin as the substrate.

A sialic acid transferase reaction in vitro was performed using GT6 strain culture medium-derived glycoprotein, BY2 strain culture medium-derived glycoprotein or asialo fetuin as the substrate. Each reactant was transferred to nitrocellulose membrane and subjected to lectin staining. As a result, the lectin staining was positive in the case where the substrate was asialo fetuin (lane 1 in FIG. 13) or GT6 strain culture medium-derived glycoprotein (lane 2 in FIG. 13), and the lectin staining was negative in the case where the substrate was BY2 strain culture medium-derived glycoprotein (lane 3, FIG. 13). From this, it is revealed that tobacco cultured cell GT6 strain culture medium-derived glycoprotein acts as the substrate in the sialic acid transferase reaction.

Comparative Example

Analysis of Glycoprotein Secreted by Non-Transformant BY2 Strain Cultured Cell (Preparation of Glycoprotein by Extracellular Secretion)

A freeze-dried culture supernatant sample was obtained by the same method as in GT6 strain except for using BY2 strain in place of GT6 strain.

(Preparation of N-Linked Sugar Chain)

N-Linked sugar chains were recovered by the same method as in GT6 strain except for using TSK gel TOYO PERAL HW-40 (produced by TOSO) gel filter column (2.5×30 cm) in place of the Sephadex G-25 super fine gel filer column (1.8×180 cm).

(Preparation of Pyridylaminated (PA) Sugar Chain)

The recovered N-linked sugar chains were PA-formed using 2-aminopyridine. The PA-sample was filtered through TSK gel TOYO PERAL HW-40 (produced by TOSO) gel filter column (2.5×30 cm) to purify the PA-sugar chains.

(Fractionation and Analysis of PA-Sugar Chain by HPLC)

The fractionation and analysis of PA-sugar chains were performed in the same manner as in GT6 strain except for using HITACHI HPLC system having a HITACHI FL Detector L-7480 in place of Jasco 880-PU HPLC having a Jasco 821-FP Intelligent Spectrofluorometer.

(Analysis of PA-Sugar Chain by Exoglycosidase Digestion)

In the enzymatic digestion reaction using N-acetylglucosaminidase (*Diplococcus pneumoniae*, Roche), each PA-sugar chain was reacted at 37° C. for 2 days in a 0.1M sodium acetate buffer (pH: 5.45) containing 3 mU of N-acetylglucosaminidase. In the enzymatic digestion reaction using α-mannosidase (Jack bean, Sigma), each PA-sugar chain was reacted at 37° C. for 2 days in a 0.1M sodium acetate buffer (pH: 4.0) containing 10 mM zinc acetate and 10 μU of α-mannosidase. Each enzymatic digestion reaction was stopped by boiling the solution at 100° C. for 3 minutes. Then, the reaction solution was centrifuged at 12,000 rpm for 10 minutes and the supernatant was subjected to HPLC. The elution time of each sample sugar chain was compared with the elution time of a known sugar chain.

(IS-MS/MS Analysis)

This analysis was performed in the same manner as in GT6 strain.

(Preparation of BY2 Strain Culture Medium-Derived PA-Sugar Chain)

Figure 14A:
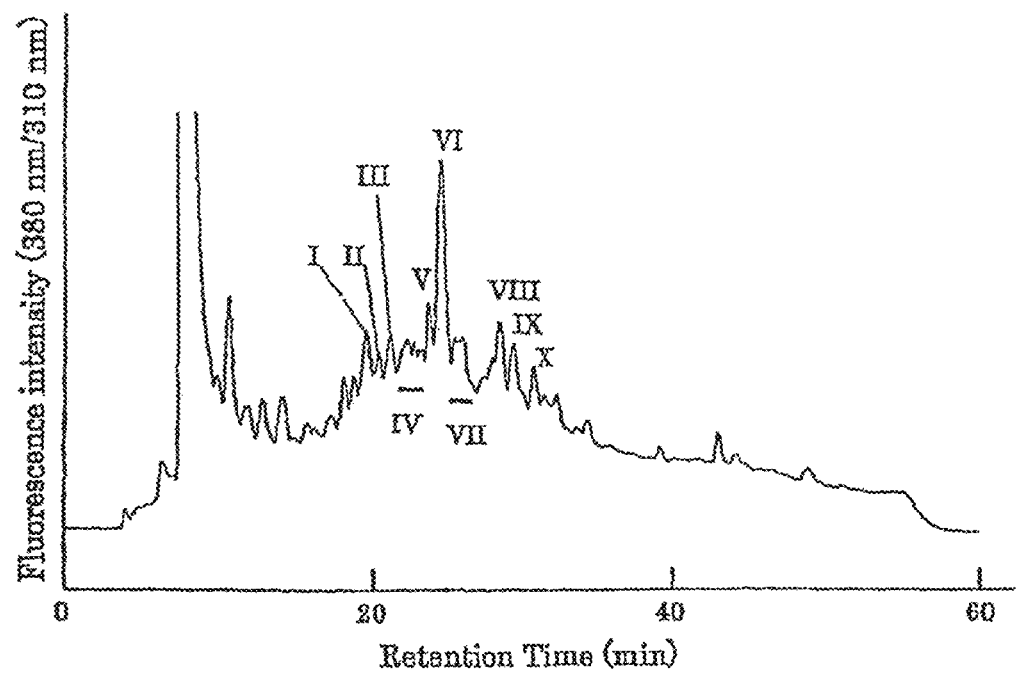
FIG. 14A is a view showing the analysis of PA-sugar salt prepared from BY2 strain culture medium by high-performance liquid chromatography.
Figure 14B:
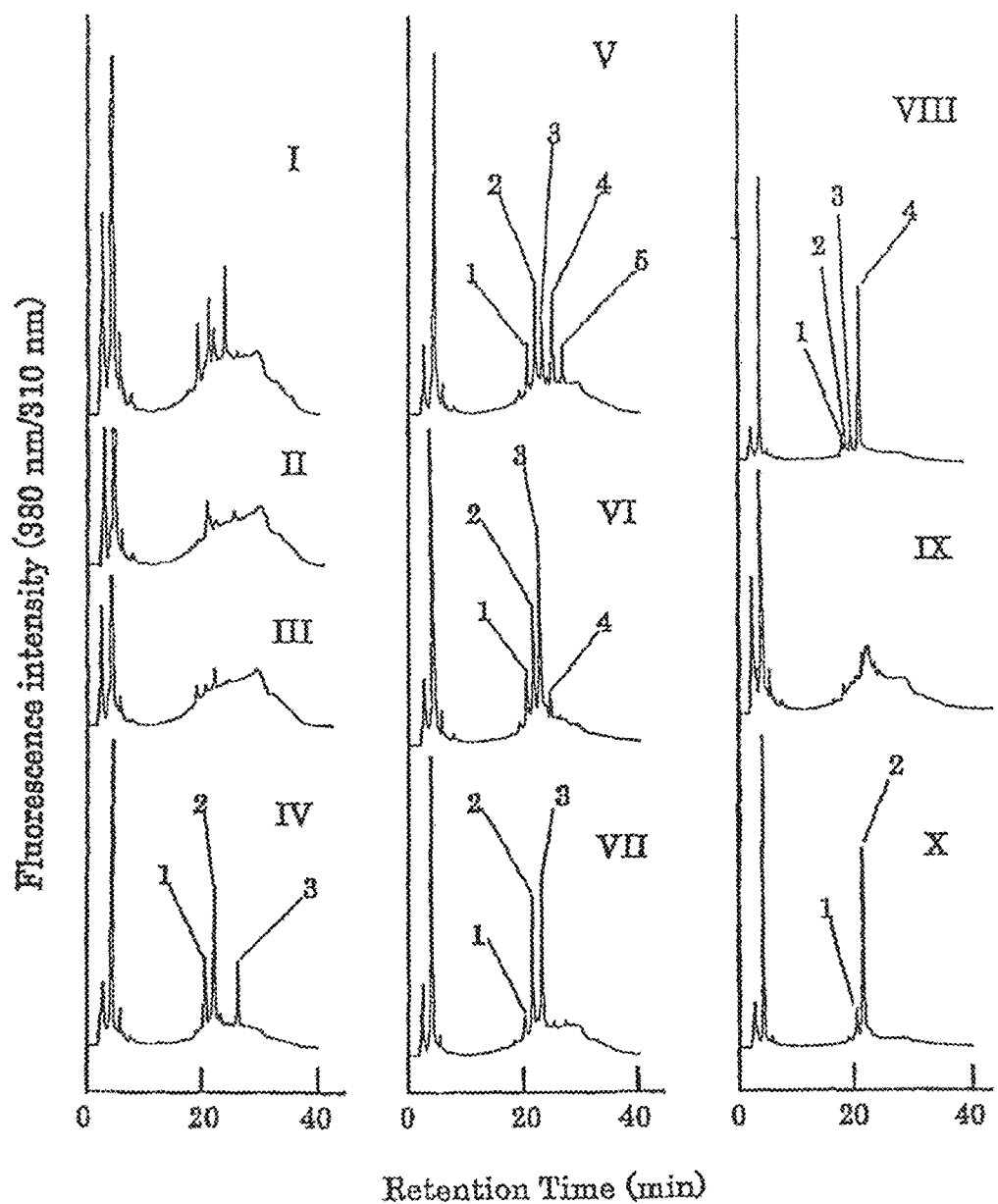
FIG. 14B is a view showing the analysis of PA-sugar salt prepared from BY2 strain culture medium by high-performance liquid chromatography.

The PA-sugar chains prepared from BY2 culture medium were also purified using RP-HPLC and SF-HPLC (FIGS. 14A and 14B). FIG. 14A shows the peaks of PA-product by RP-HPLC. After the recovery, each fraction (I to X) was subjected to SF-HPLC (FIG. 14B).

Figure 15A:
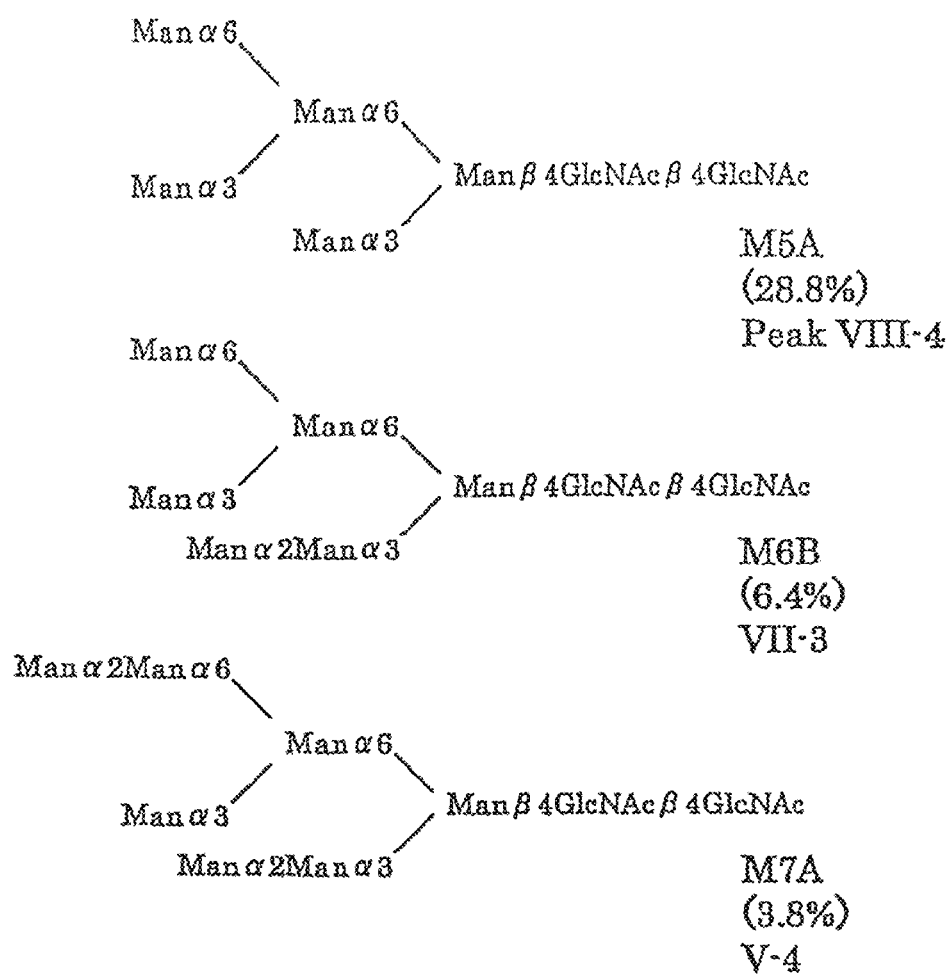
FIG. 15A is a view showing the structures and analysis results of sugar chains in the glycoprotein secreted in the GT6 strain culture medium. The numerals in parentheses in the Figure show the molar ratio of sugar chain having each structure shown in the Figure.
Figure 15B:
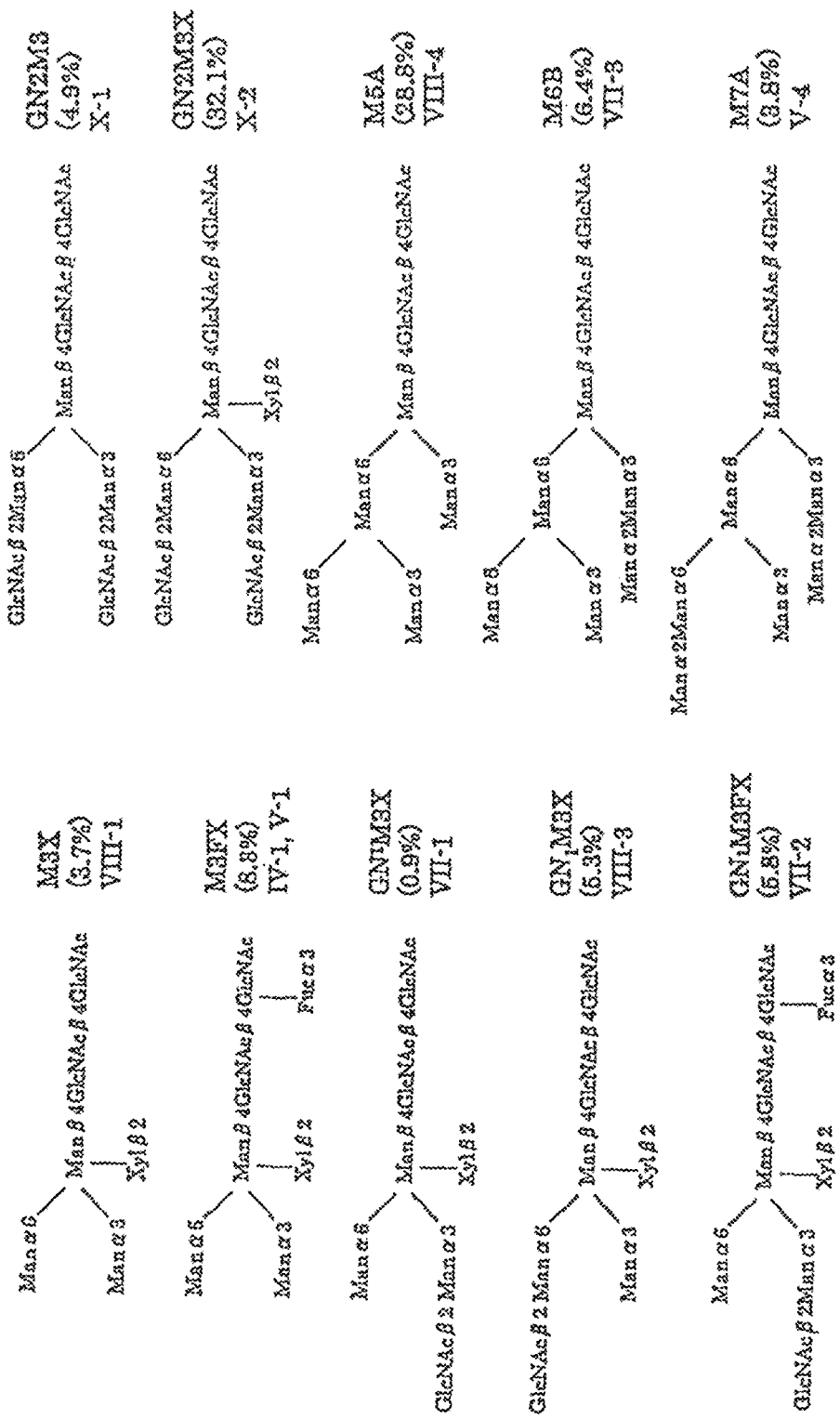
FIG. 15B is a view showing the structures and analysis results of sugar chains in the glycoprotein secreted in the GT6 strain culture medium. The numerals in parentheses in the Figure show the molar ratio of sugar chain having each structure shown in the Figure.

In the fractions (I, II and III) shown in FIG. 14A, N-linked sugar chain was not detected by SF-HPLC analysis. This was verified because in IS-MS/MS analysis, signals agreeing with m/z 299.33 (GlcNAc-PA) and m/z 502.52 (GlcNAc$_2$-PA) were not obtained. The peaks of fractions IV to X were analyzed by SF-HPLC, as a result, 21 peaks were obtained (see, FIG. 14B). FIGS. 15A and 15B show analyzed N-linked sugar chain structures.

(Structural Analysis of BY2 Strain Culture Medium-Derived PA-Sugar Chain)

As a result of IS-MS/MS analysis of the peaks V-4, VII-3 and VIII-4 shown in FIG. 14B, the molecular weights (m/z) were 1639.0, 1476.5 and 1314.5, respectively and, on considering the elution sites in SF-HPLC together, the sugar chain structures present in the peaks agreed with PA-high mannose sugar chain Man$_7$GlcNAc$_2$-PA, Man$_6$GlcNAc$_2$-PA and Man$_5$GlcNAc$_2$-PA, respectively (the data are not shown).

Also, as a result of SF-HPLC analysis, the α-mannosidase digestion product of sugar chain of each peak agreed with Man GlcNAc$_2$-PA (M1) (the data are not shown). When the isomers M7A, M7B and M7D of Man$_7$GlcNAc$_2$-PA were compared, the elution site of the peak V-4 agreed with the elution site of M7A. Among the isomers M6B and M6C of Man$_6$GlcNAc$_2$-PA, the peak VII-3 agreed with M6B. Also, the isomer M5A of Man$_5$GlcNAc$_2$-PA and the peak VIII-4 agreed.

From these data, the peaks V-4, VII-3 and VIII-4 shown in FIG. 14B were, as shown in FIG. 15A, α-D-Man-(1→2)-α-D-Man-(1→6) [α-D-Man-(1→3)] α-D-Man-(1→6) [α-D-Man-(1→2)-α-D-Man-(1→3)] β-D-Man-(1→4)-β-D-GlcNAc-(1→4)-GlcNAc-PA (M7A), α-D-Man-(1→6) [α-D-Man-(1→3)] α-D-Man-(1→6) [α-D-Man(1→2)-α-D-Man-(1→3)] β-D-Man-(1-4)-β-D-GlcNAc-(1→4)-GlcNAc-PA (M6A), and α-D-Man-(1→6) [α-D-Man-(1→3)] α-D-Man-(1-6) [α-D-Man-(1→3)] β-D-Man-(1→4)-β-D-GlcNAc-(1→4)-GlcNAc-PA (M5A). In the figure, the numerals in parentheses indicate the molar ratio of sugar chain having each structure shown in the Figure.

Figure 17:
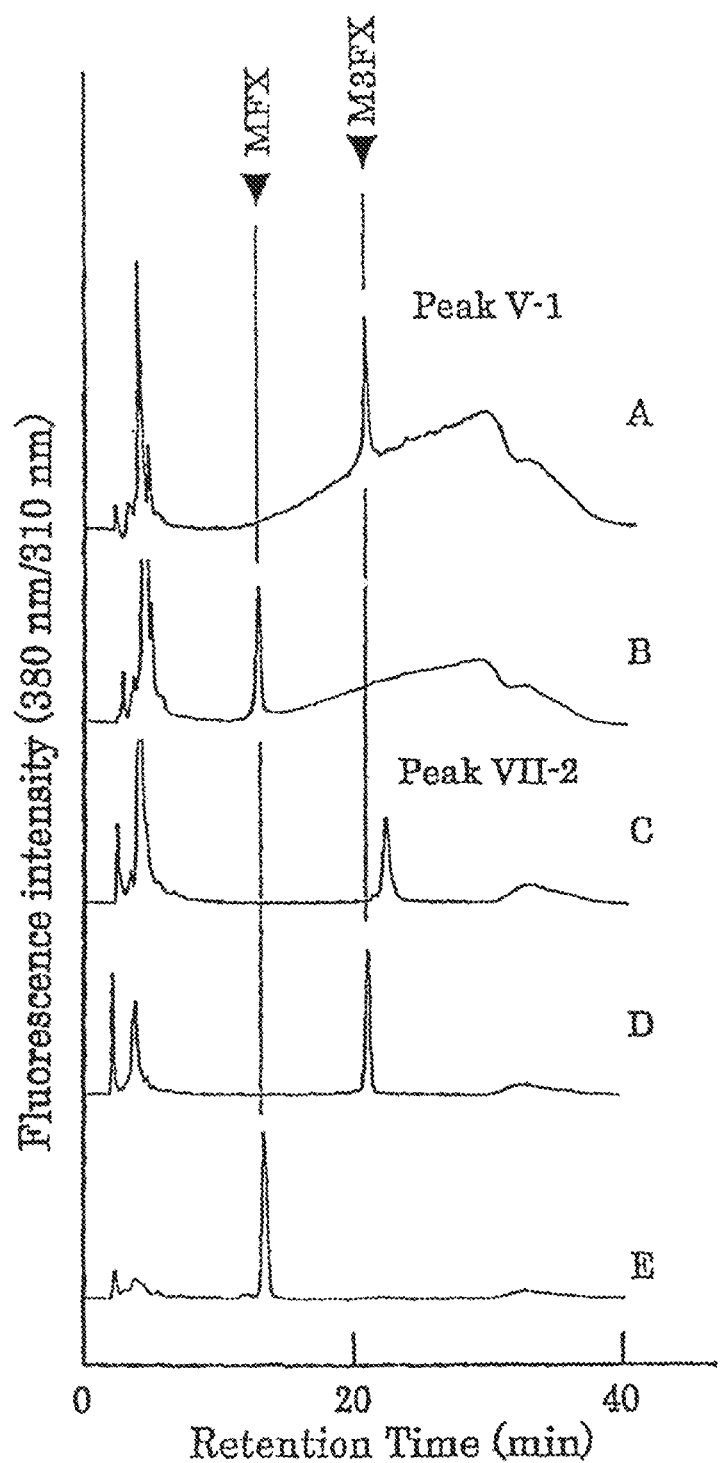
FIG. 17 is a view showing the analysis of PA-sugar chain prepared from BY2 strain culture medium and the exoglycosidase digestion product thereof by high-performance liquid chromatography.

The molecular weight (m/z 1267.5) determined by the IS-MS analysis of the peaks IV-1 and V-1 shown in FIG. 14B agreed with the calculated value of Man$_3$XylFucGlcNAc$_2$-PA (M3FX: 1267.19). Also, the elution site in HPLC completely agreed with M3FX standard product on the two-dimensional sugar chain map. Furthermore, as a result of SF-HPLC analysis and IS-MS/MS analysis, the α-mannosidase digestion product of sugar chain of each peak agreed with the calculated value of ManXylFucGlcNAc$_2$-PA (MFX: 942.91) (see, FIGS. 17A and 17B).

From these data, the peaks IV-1 and V-1 shown in FIG. 14B were, as shown in FIG. 15B, α-D-Man-(1→6) [α-D-Man-(1→3)] [β-D-Xyl-(1→2)] β-D-Man-(1-4)-β-D-GlcNAc-(1→4)-[α-L-Fuc-(1→3)]GlcNAc-PA (M3FX).

Figure 16:
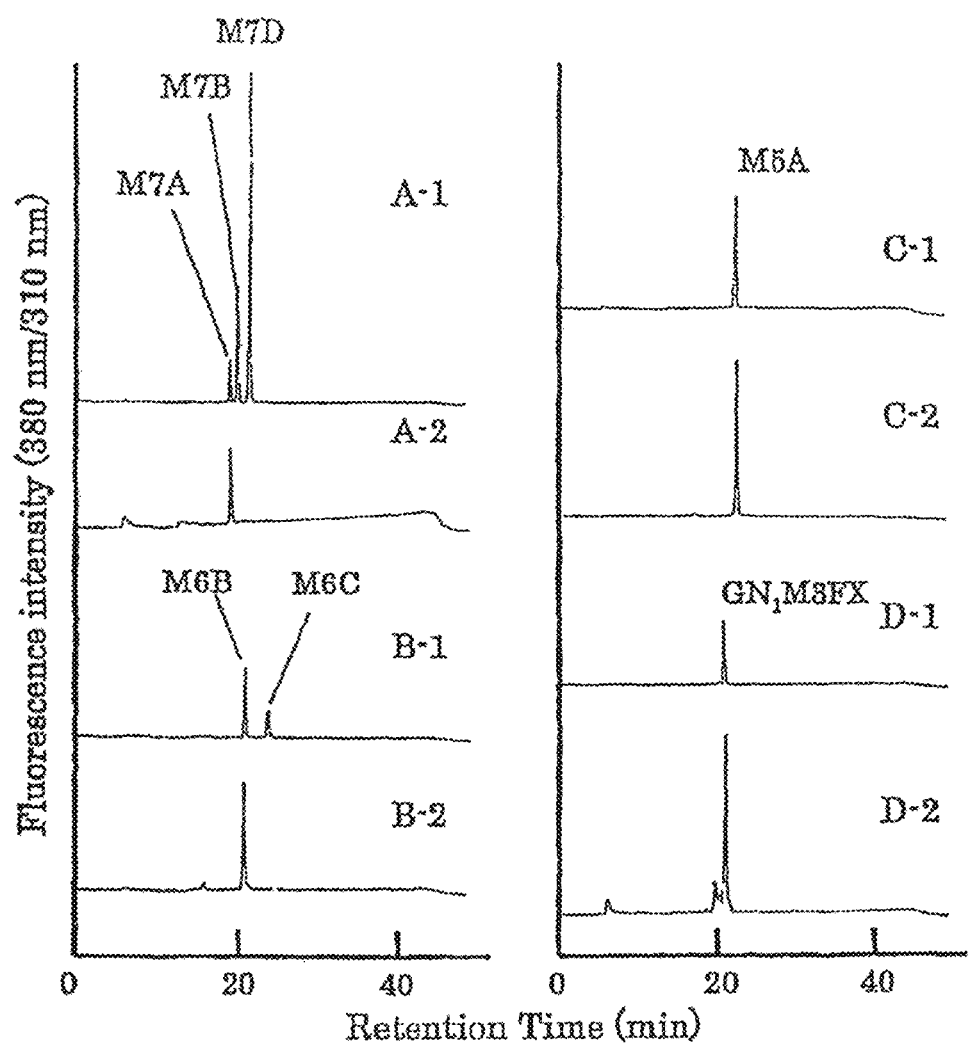
FIG. 16 is a view showing the analysis of PA-sugar chain prepared from BY2 strain culture medium.

The molecular weight (m/z 1417.0) determined by the IS-MS analysis of the peak VII-2 shown in FIG. 14B agreed with the calculated value of GlcNAcMan$_3$XylFucGlcNAc$_2$-PA (GNM3FX: 1470.38). Also, as a result of SF-HPLC analysis and IS-MS/MS analysis, the N-acetylglucosaminidase digestion product of sugar chain of the peak agreed with Man$_3$XylFucGlcNAc$_2$-PA (M3FX: 1267.19). Furthermore, after the digestion by α-mannosidase, the SF-HPLC analysis and IC-MS/MS analysis revealed that the product agreed with ManXylFucGlcNAc$_2$-PA (MFX: 942.91) (C to E in FIG. 17). On the two-dimensional sugar chain map, the elution site in RP-HPLC of the peak VII-2 (D-2 in FIG. 16) completely agreed with the standard product GN$^1$M3FX, β-D-GlcNAc-(1→2)-α-D-Man-(1-1.6) [α-D-Man-(1→3)] [β-D-Xyl-(1→2)] fi-D-Man-(1→4)-β-D-GlcNAc-(1→4)-[α-L-Fuc-(1-3)]GlcNAc-PA (D-1 in FIG. 16).

From these data, the peak VII-2 was, as shown in FIG. 15B, β-D-GlcNAc-(1→2)-α-D-Man-(1→6) [α-D-Man-(1→3)] [β-D-Xyl-(1→2)] β-D-Man-(1→4)-β-D-GlcNAc-(1→4)-[α-L-Fuc-(1→3)]GlcNAc-PA (GN$^1$M3FX).

Figure 18A:
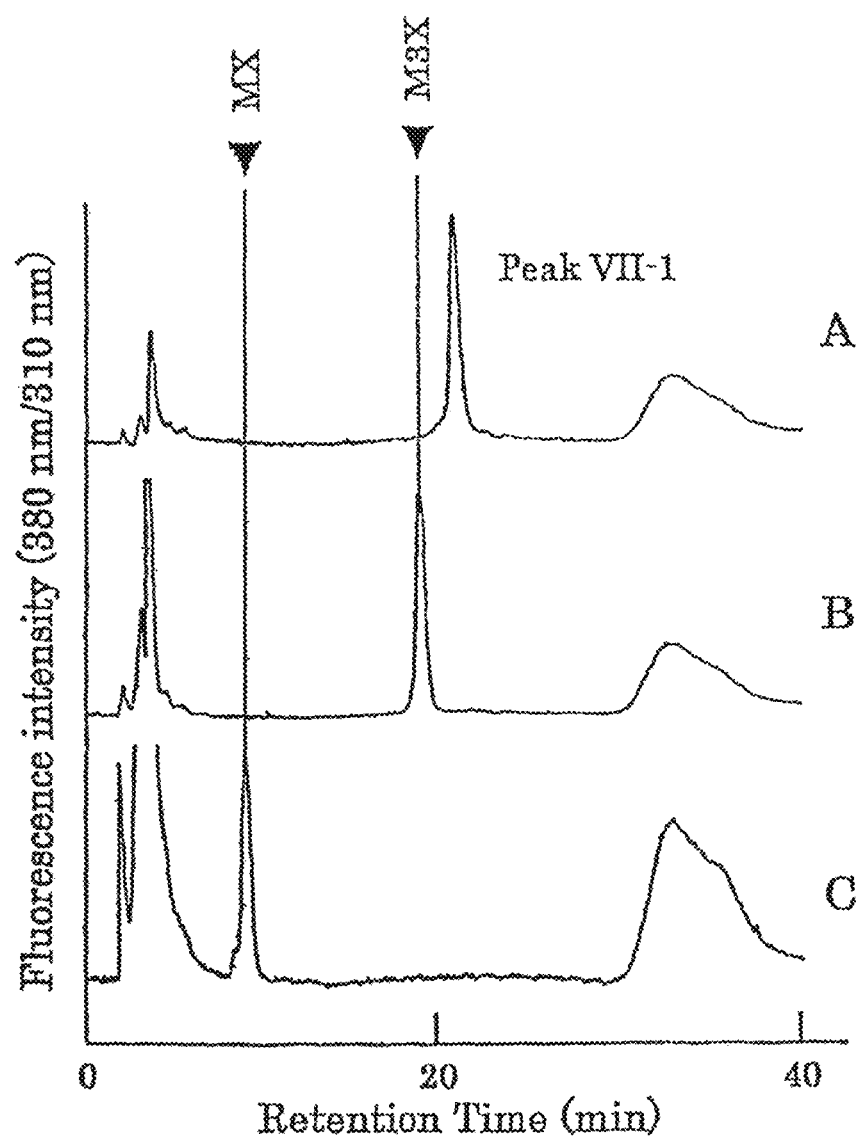
FIG. 18A is a view showing the analysis of PA-sugar chain prepared from BY2 strain culture medium and the exoglycosidase digestion product thereof by high-performance liquid chromatography.

The molecular weight (m/z 1324.0) of the peaks VII-1 and VIII-3 shown in FIG. 14B agreed with the calculated value of GlcNAcMan$_3$XylGlcNAc$_2$-PA (GNM3FX: 1324.24). Also, as a result of SF-HPLC analysis and IS-MS/MS analysis, the N-acetylglucosaminidase digestion product of the peak VIII-1 agreed with Man$_3$XylGlcNAc$_2$-PA (M3X: 1121.05) (B in FIG. 18A). Furthermore, after the digestion by α-mannosidase, the SF-HPLC analysis and IC-MS/MS analysis revealed that the product agreed with ManXylGlcNAc$_2$-PA (MX: 796.77) (C in FIG. 18A). As the structure of GNM3X, two isomer types are considered, that is, α-D-Man-(1-'6) [β-D-GlcNAc-(1→2)-α-D-Man-(1→3)] [β-D-Xyl-(1→2)] β-D-Man-(1→4)-β-D-GlcNAc-(1→4)-GlcNAc-PA (GN$_1$M3X) and β-D-GlcNAc-(1→2)-α-D-Man-(1→6) [α-D-Man-(1→3)] [β-D-Xyl-(1→2)] β-D-Man-(1→4)-β-D-GlcNAc-(1→4)-GlcNAc-PA (GN$^1$M3X). On the ODS column, it has been reported that GN$_1$M3X elutes in advance of GN$^1$M3X. When the elution sites of the peaks VII-1 and VIII-3 are considered, as shown in FIG. 15B, the peak VII-1 was α-D-Man-(1→6) [β-D-GlcNAc-(1→2)-α-D-Man-(1→3)][β-D-Xyl-(1→2)] VD-Man-(1→4) (GN$_1$M3X) and the peak VIII-3 was β-D-GlcNAc-(1→2)-α-D-Man-(1→6) [α-D-Man-(1→3)] [β-D-Xyl-] β-D-Man-(1→4)-β-D-GlcNAc-(1→4)-GlcNAc-PA (GN$^1$M3X).

The elution site of the peak X-1 shown in FIG. 14B in HPLC completely agreed with the standard GN2M3 (1395.32) on the two-dimensional sugar chain map. Also, as a result of SF-HPLC analysis and IS-MS/MS analysis, the N-acetylglucosaminidase digestion product of sugar chain of the peak agreed with Man$_3$GlcNAc$_2$-PA (M3: 988.94). Furthermore, after the digestion by α-mannosidase, the SF-HPLC analysis and IC-MS/MS analysis revealed that the product agreed with ManGlcNAc$_2$-PA (M1: 664.66) (the data are not shown). From these results, the peak X-1 was, as shown in FIGS. 15A and 15B, β-D-GlcNAc-(1→6) [β-D-GlcNAc-(1→2)-α-D-Man-(1→3)] β-D-Man-(1→4)-β-D-GlcNac-(1→4)-GlcNAc-PA (GN2M3).

Figure 18B:
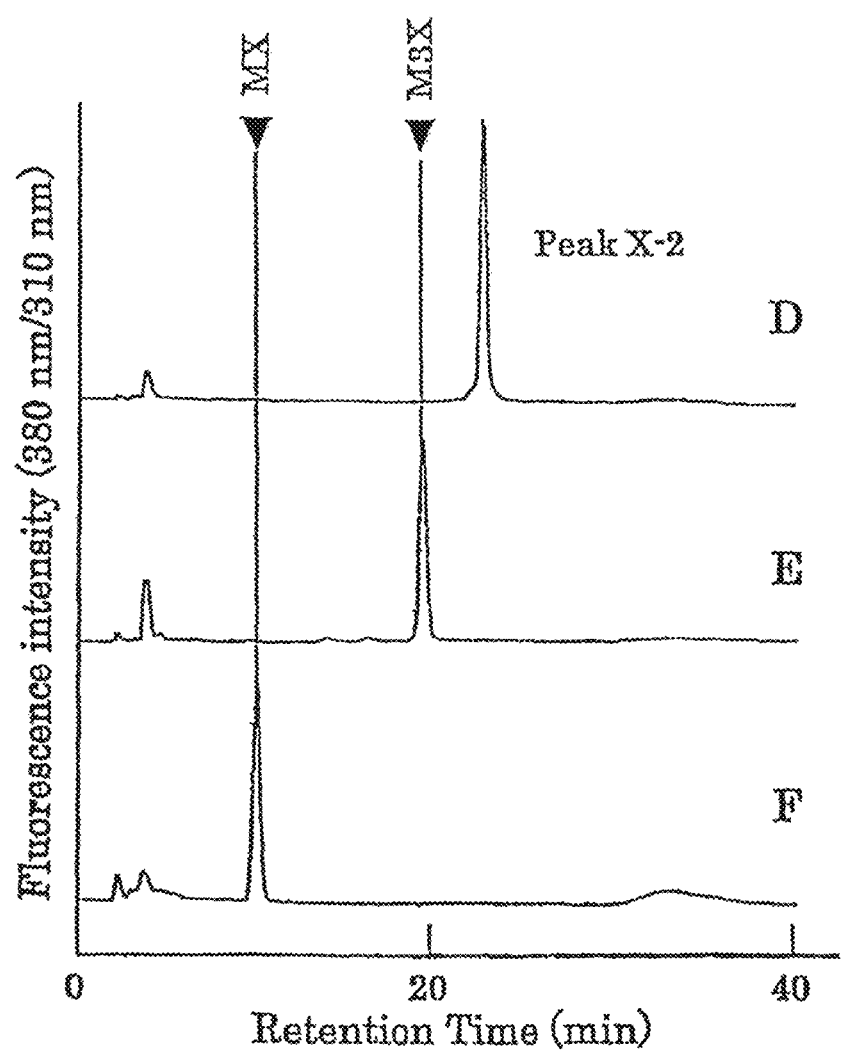
FIG. 18B is a view showing the analysis of PA-sugar chain prepared from BY2 strain culture medium and the exoglycosidase digestion product thereof by high-performance liquid chromatography.

The molecular weight (m/z 1529.5) of the peak X-2 shown in FIG. 14B agreed with the calculated value of GlcNAc$_2$Man$_3$XylGlcNAc$_2$-PA (GN2M3FX: 1527.43). Also, the elution site in HPLC completely agreed with the M3FX standard product on the two-dimensional sugar chain map. Furthermore, the elution site of the α-mannosidase digestion product of sugar chain of this peak was not changed by the HPLC analysis. However, as a result of the SF-HPLC analysis and IC-MS/MS analysis, the N-acetylglucosaminidase digestion product agreed with Man$_2$XylGlcNAc$_2$-PA (M3X: 1121.05) (B in FIG. 18B). After further digestion by α-mannosidase, the SF-HPLC analysis and IC-MS/MS analysis revealed that the product agreed with ManXylGlcNAc$_2$-PA (MX: 796.77) (C in FIG. 18A). From these data, the peak X-2 was, as shown in FIG. 15B, β-D-GlcNAc-(1→2)-α-D-Man-(1→6) [β-D-GlcNAc-(1→2)-α-D-Man-(1→3)] [β-D-Xyl-(1→2)] β-D-Man-(1→4)-β-D-GlcNAc-(1→4)-GlcNAc-PA (GN2M3X).

Other peaks IV-2, IV-3, V-2, V-3, V-5, VI-1, VI-2, VI-3, VI-4, VIII-2 and IX shown in FIG. 14B were not an N-linked sugar chain, because as a result of the IS-MS/MS analysis, signals agreeing with m/z 299.33 (GlcNAc-PA) and m/z 502.52 (GlcNAc$_2$-PA) were not obtained.

4. Secretion of Horse Radish Peroxidase (HRP)

Figure 19:
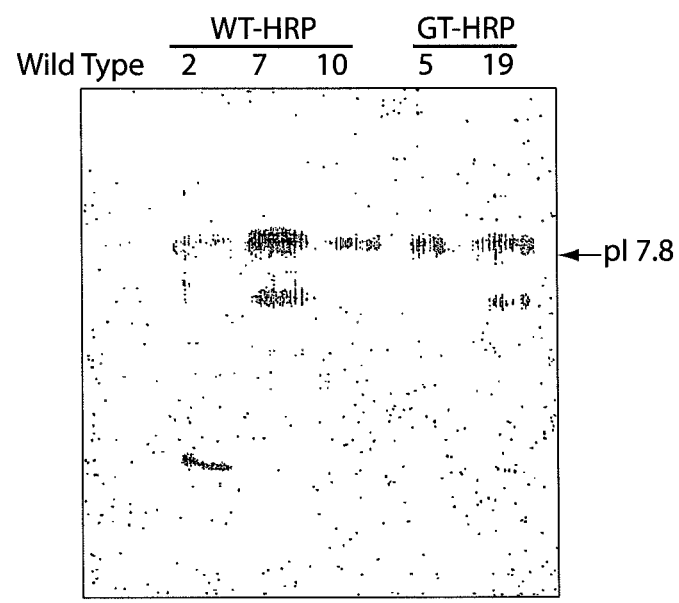
FIG. 19 is a photograph showing the results of isoelectric focusing electrophoresis. Proteins in the spent media of cultured tobacco cells were analyzed by isoelectric focusing and stained for peroxidase activity. Wild Type denotes BY2 strain. WT-HRP denotes transformant of BY2 strain with HRP. GT-HRP denotes the transformant of GT6 strain with HRP gene.
Figure 20:
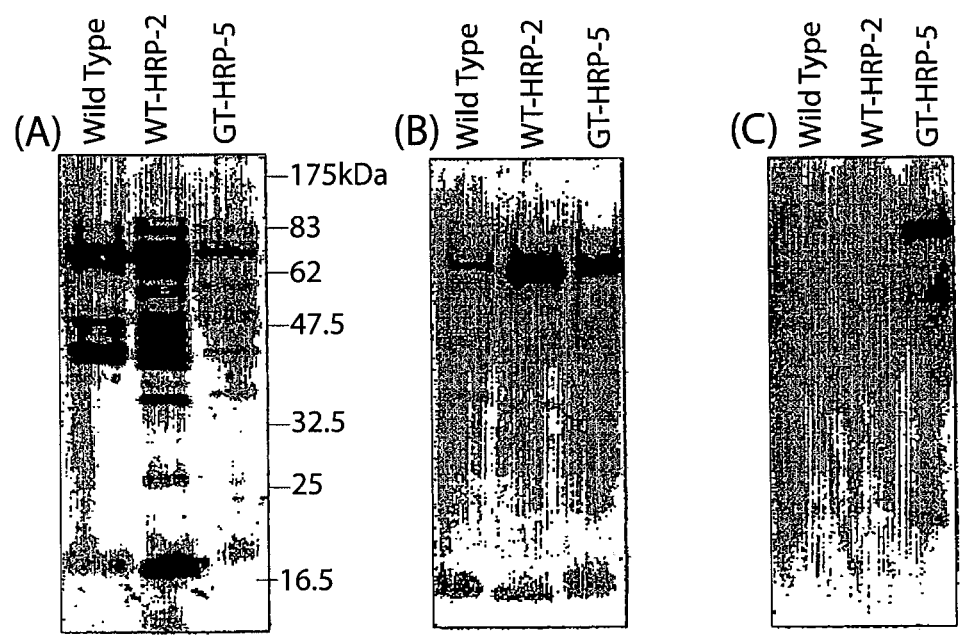
FIG. 20 is a photograph showing the results of lectin staining of proteins in the spent media of transgenic cultured tobacco cells. Proteins were fractionated by SDS-PAGE and stained with Coomassie brilliant blue (A), or transferred to nitrocellulose membrane and treated with ConA(B), and RCA120(C). Wild Type denotes BY2 strain. WT-HRP-2 denotes one of the transformants of BY2 strain with HRP gene. GT-HRP-5 denotes one of the transformants of GT6 strain with HRP gene.

A foreign gene, horseradish peroxidase gene, which was obtained from 35S-Cla (Kawaoka et al., J. Ferment. Bioeng., 78, 49-53 (1994)), was inserted at Hind III and SacI site of vector pBI101 HmB (Akama et al., Plant Cell Rep. 12, 7-11 (1992)) and introduced into GT6 Strain. After cultivating the obtained clones of GT6 Strain (GT-HRP-5, GT-HRP-19), the supernatant was collected, and subjected to a standard isoelectric focusing electrophoresis. As a result, as indicated in FIG. 19, electrophoresis band of pI 7.8 of HRP was detected in the supernatant of clones GT-HRP-5, GT-HRP-19, and thus confirmed that an foreign protein was also secreted from the plant cell transformed with the GalT gene. Further, FIG. 20 indicates the results of lectin staining of secreted proteins by clone GT-HRP-5, separated by standard SDS-PAGE electrophoresis as described above. RCA120 staining indicates that GT-HRP-5 has a positive signal (FIG. 20(*c*)), and thus it was indicated that secreted HRP had a galactose added sugar chain structure.

INDUSTRIAL APPLICABILITY

According to the present invention, a method for the secretory production of a heterologous glycoprotein having a human-type sugar chain using a plant cell, a plant cell which can secrete this glycoprotein, and a glycoprotein having a human-type sugar chain which is secreted by a plant cell. The glycoprotein of the present invention has a human-type sugar chain and therefore, is free of antigenicity and is useful for the administration to animals including human.

What is claimed is:

1. A method for producing a secretory glycoprotein having a human-type sugar chain from a transgenic plant cell, the method comprising:
   providing a transgenic plant cell that comprises a first heterologous nucleic acid sequence encoding a β1,4-galactosyltransferase, and a second heterologous nucleic acid sequence encoding a glycoprotein that is heterologous to the plant cell,
   culturing the transgenic plant cell in a culture medium to allow production and secretion of the glycoprotein, which contains an N-glycan having a galactose residue linked to a non-reducing terminal acetylglucosamine residue;
   isolating the glycoprotein from the culture medium; and
   contacting the isolated glycoprotein with a sialic acid transferase to add a sialic acid residue attached to the galactose residue in the N-glycan.

2. The method of claim 1, wherein in the transgenic plant cell, the expression of an endogenous β1,2-xylosyltransferase, α1,3-fucosyltransferase, or both is inhibited or a gene encoding the endogenous β1,2-xylosyltransferase or α1,3-fucosyltransferase is mutated.

3. The method of claim 2, wherein the transgenic plant cell has the endogenous gene encoding the β1,2-xylosyltransferase or the endogenous α1,3-fucosyltransferase inactivated.

4. The method of claim 2, wherein the transgenic plant cell has the endogenous genes encoding both the β1,2-xylosyltransferase and the α1,3-fucosyltransferase inactivated.

5. The method of claim 1, wherein the culture medium comprises an agent that increases the concentration of the glycoprotein in the culture medium, and wherein the agent is polyvinylpyrrolidone (PVP).

6. The method of claim 5, wherein the culture medium further comprises a protease inhibitor.

7. The method of claim 1, wherein the transgenic plant cell is in a cultured plant tissue, a cultured plant organ, or a whole plant.

8. The method of claim 1, wherein the transgenic plant cell is a cell of Solanaceae, Gramineae, Cruciferae, Rosaceae, Leguminosae, Cucurbitaceae, Labiatae, Liliaceae, Chenopodiaceae, or Umbelliferae.

9. The method of claim 8, wherein the transgenic plant cell is a tobacco cell.

10. The method of claim 1, wherein the heterologous glycoprotein is an enzyme, a hormone, a cytokine, an antibody, a vaccine antigen, a receptor, or a serum protein.

11. The method of claim 1, wherein the β1,4-galactosyltransferase is a human β1,4-galactosyltransferase.

12. The method of claim 11, wherein the human β1,4-galactosyltransferase comprises the amino acid sequence of SEQ ID NO:6.

13. The method of claim 1, wherein the providing step is performed by:
   introducing into a plant cell the first heterologous nucleic acid sequence and the second heterologous nucleic acid sequence; thereby producing the transgenic plant cell.

14. The method of claim 13, wherein the providing step further comprises inactivating the endogenous β1,2-xylosyltransferase, α1,3-fucosyltransferase, or both in the plant cell.

15. The method of claim 14, wherein the inactivating step is performed by chemical mutagenesis, site-directed mutagenesis, or a tagging method to inactivate the gene encoding the β1,2-xylosyltransferase or α1,3-fucosyltransferase.

* * * * *